(12) United States Patent
Crapo et al.

(10) Patent No.: US 8,980,574 B2
(45) Date of Patent: Mar. 17, 2015

(54) METHOD FOR AMELIORATING RADIATION EXPOSURE EFFECTS WITH ALPHA-1 ANTITRYPSIN

(76) Inventors: James D. Crapo, Englewood, CO (US); A. Mario Q. Marcondes, Seattle, WA (US); H. Joachim Deeg, Seattle, WA (US)

( * ) Notice: Subject to any disclaimer, the term of this patent is extended or adjusted under 35 U.S.C. 154(b) by 0 days.

(21) Appl. No.: 14/004,057

(22) PCT Filed: Mar. 9, 2012

(86) PCT No.: PCT/US2012/028568
§ 371 (c)(1),
(2), (4) Date: Dec. 20, 2013

(87) PCT Pub. No.: WO2012/125487
PCT Pub. Date: Sep. 20, 2012

(65) Prior Publication Data
US 2014/0107042 A1 Apr. 17, 2014

Related U.S. Application Data

(60) Provisional application No. 61/523,759, filed on Aug. 15, 2011, provisional application No. 61/452,026, filed on Mar. 11, 2011.

(51) Int. Cl.
*C12Q 1/37* (2006.01)
*A61K 38/55* (2006.01)
*A61K 38/57* (2006.01)

(52) U.S. Cl.
CPC ............... *A61K 38/57* (2013.01); *A61K 38/55* (2013.01)
USPC .......................................... 435/23; 424/185.1

(58) Field of Classification Search
USPC ................... 435/23; 424/185.1; 514/21.2
See application file for complete search history.

(56) References Cited

U.S. PATENT DOCUMENTS

| | | | |
|---|---|---|---|
| 6,127,145 A * | 10/2000 | Sutliff et al. | 435/69.1 |
| 6,645,934 B1 * | 11/2003 | Rodemann et al. | 530/300 |
| 2003/0105027 A1 | 6/2003 | Rosenblum | |
| 2009/0214467 A1 | 8/2009 | Shakov et al. | |
| 2009/0289182 A1 | 11/2009 | Pevsner | |
| 2011/0237496 A1* | 9/2011 | Nathan et al. | 514/1.4 |

OTHER PUBLICATIONS

Park et al., Identification and Characterization of Human Endometase {Matrix Metalloproteinase-26) from Endometrial Tumor. J Bioi Chern, Jul. 7, 2000, vol. 275, No. 27, pp. 20540-20544. Especially_p. 20540, col. 2, p. 20543, col. 2.
Rana et al., Radiation-induced biomarkers for the detection and assessment of absorbed radiation doses. J Pharm Bioallied Sci, Jui.-Sep. 2010, Radiation-induced biomarkers for the detection and assessment of absorbed radiation dose, vol. 2, No. 3, pp. 189-196.
Herodin et al., Radioprotective Effect of an Acute Non-specific Inflammation in Mice. International Journal of Radiation Biology. Mar. 1987, vol. 51, No. 3, pp. 549-559.
International Search Report and Written Opinion for PCT/US2012/025868, dated Jun. 22, 2012.

* cited by examiner

*Primary Examiner* — Ralph Gitomer

(57) ABSTRACT

Embodiments described herein relate to compositions, methods and uses for alpha-1 antitrypsin (AAT) or derivatives or analogs or peptides or mutants thereof for treating a subject exposed to radiation. In certain embodiments, AAT or derivatives thereof or analogs thereof can be used to modulate adverse effects of radiation therapy on subjects undergoing treatment for cancer. In other embodiments, compositions disclosed herein can be used for treating a subject having been exposed to non-therapeutic or accidental radiation. Some embodiments reported herein concern compositions and methods for enhancing radiotherapy. Certain embodiments relate to methods and compositions for preventing or reducing radiation exposure-induced cellular damage in a subject.

27 Claims, 14 Drawing Sheets

SEQUENCE LISTING

<160> NUMBER OF SEQ ID NOS: 44

<210> SEQ ID NO 1
<211> LENGTH: 394
<212> TYPE: PRT
<213> ORGANISM: Homo sapiens

<400> SEQUENCE: 1

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
```

```
                    85                  90                  95
Gln Glu Leu Leu Arg Thr Leu Asn Gln Pro Asp Ser Gln Leu Gln Leu
                100                 105                 110

Thr Thr Gly Asn Gly Leu Phe Leu Ser Glu Gly Leu Lys Leu Val Asp
            115                 120                 125

Lys Phe Leu Glu Asp Val Lys Leu Tyr His Ser Glu Ala Phe Thr
        130                 135                 140

Val Asn Phe Gly Asp Thr Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
                180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
        290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 2
<211> LENGTH: 5
<212> TYPE: PRT
<213> ORGANISM: Artificial Sequence
<220> FEATURE:
<223> OTHER INFORMATION: synthetic peptide

<400> SEQUENCE: 2

Phe Val Phe Leu Met
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic peptide
```

```
<400> SEQUENCE: 3

Phe Val Phe Ala Met
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Phe Val Ala Leu Met
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide

<400> SEQUENCE: 5

Phe Val Phe Leu Ala
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Phe Leu Val Phe Ile
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Phe Leu Met Ile Ile
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Phe Leu Phe Val Leu
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic peptide
```

-continued

<400> SEQUENCE: 9

Phe Leu Phe Val Val
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic peptide

<400> SEQUENCE: 10

Phe Leu Phe Leu Ile
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic peptide

<400> SEQUENCE: 11

Phe Leu Phe Phe Ile
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic peptide

<400> SEQUENCE: 12

Phe Leu Met Phe Ile
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide

<400> SEQUENCE: 13

Phe Met Leu Leu Ile
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic peptide

<400> SEQUENCE: 14

Phe Ile Ile Met Ile
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic peptide

<400> SEQUENCE: 15

```
Phe Leu Phe Cys Ile
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic peptide

<400> SEQUENCE: 16

Phe Leu Phe Ala Val
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Phe Val Tyr Leu Ile
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic peptide

<400> SEQUENCE: 18

Phe Ala Phe Leu Met
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic peptide

<400> SEQUENCE: 19

Ala Val Phe Leu Met
1               5

<210> SEQ ID NO 20
<211> LENGTH: 10
<212> TYPE: PRT
<213> ORGANISM: Artificial Sequence
<220> FEATURE:
<223> OTHER INFORMATION: synthetic peptide

<400> SEQUENCE: 20

Leu Ser Gly Val Thr Glu Glu Ala Pro Leu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: synthetic peptide

<400> SEQUENCE: 21
```

```
Lys Leu Ser Lys Ala Val His Lys Ala Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic peptide

<400> SEQUENCE: 22

Leu Thr Ile Asp Glu Lys Gly Thr Glu Ala
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic peptide

<400> SEQUENCE: 23

Ala Gly Ala Met Phe Leu Glu Ala Ile Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic peptide

<400> SEQUENCE: 24

Met Ser Ile Pro Pro Glu Val Lys Phe Asn
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Lys Pro Phe Val Phe Leu Met Ile Glu Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic peptide

<400> SEQUENCE: 26

Asn Thr Lys Ser Pro Leu Phe Met Gly Lys
1               5                   10

<210> SEQ ID NO 27
<211> LENGTH: 7
<212> TYPE: PRT
<213> ORGANISM: Artificial Sequence
<220> FEATURE:
<223> OTHER INFORMATION: synthetic peptide

<400> SEQUENCE: 27

Val Val Asn Pro Thr Gln Lys
```

```
<210> SEQ ID NO 28
<211> LENGTH: 10
<212> TYPE: PRT
<213> ORGANISM: Artificial Sequence
<220> FEATURE:
<223> OTHER INFORMATION: synthetic peptide

<400> SEQUENCE: 28

Gly Ala Asp Leu Ser Gly Val Thr Glu Glu
1               5                   10

<210> SEQ ID NO 29
<211> LENGTH: 10
<212> TYPE: PRT
<213> ORGANISM: Artificial Sequence
<220> FEATURE:
<223> OTHER INFORMATION: synthetic peptide

<400> SEQUENCE: 29

Ala Pro Leu Lys Leu Ser Lys Ala Val His
1               5                   10

<210> SEQ ID NO 30
<211> LENGTH: 10
<212> TYPE: PRT
<213> ORGANISM: Artificial Sequence
<220> FEATURE:
<223> OTHER INFORMATION: synthetic peptide

<400> SEQUENCE: 30

Lys Ala Val Leu Thr Ile Asp Glu Lys Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: synthetic peptide

<400> SEQUENCE: 31

Thr Glu Ala Ala Gly Ala Met Phe Leu Glu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: synthetic peptide

<400> SEQUENCE: 32

Arg Ile Pro Val Ser Ile Pro Pro Glu Val
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic peptide

<400> SEQUENCE: 33

Lys Phe Asn Lys Pro Phe Val Phe Leu Met
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: synthetic peptide

<400> SEQUENCE: 34

Ile Glu Gln Asn Thr Lys Ser Pro Leu Phe
1               5                   10

<210> SEQ ID NO 35
<211> LENGTH: 10
<212> TYPE: PRT
<213> ORGANISM: Artificial Sequence
<220> FEATURE:
<223> OTHER INFORMATION: synthetic peptide

<400> SEQUENCE: 35

Met Gly Lys Val Val Asn Pro Thr Gln Lys
1               5                   10

<210> SEQ ID NO 36
<211> LENGTH: 22
<212> TYPE: PRT
<213> ORGANISM: Artificial Sequence
<220> FEATURE:
<223> OTHER INFORMATION: synthetic peptide

<400> SEQUENCE: 36

Leu Glu Ala Ile Pro Met Ser Ile Pro Pro Glu Val Lys Phe Asn Lys
1               5                   10                  15

Pro Phe Val Phe Leu Met
            20

<210> SEQ ID NO 37
<211> LENGTH: 20
<212> TYPE: PRT
<213> ORGANISM: Artificial Sequence
<220> FEATURE:
<223> OTHER INFORMATION: synthetic peptide

<400> SEQUENCE: 37

Leu Glu Ala Ile Pro Met Ser Ile Pro Pro Glu Val Lys Phe Asn Lys
1               5                   10                  15

Pro Phe Val Phe
            20

<210> SEQ ID NO 38
<211> LENGTH: 80
<212> TYPE: PRT
<213> ORGANISM: Artificial Sequence
<220> FEATURE:
<223> OTHER INFORMATION: synthetic peptide

<400> SEQUENCE: 38

Gly Ala Asp Leu Ser Gly Val Thr Glu Glu Ala Pro Leu Lys Leu Ser
1               5                   10                  15

Lys Ala Val His Lys Ala Val Leu Thr Ile Asp Glu Lys Gly Thr Glu
                20                  25                  30

Ala Ala Gly Ala Met Phe Leu Glu Arg Ile Pro Val Ser Ile Pro Pro
            35                  40                  45

Glu Val Lys Phe Asn Lys Pro Phe Val Phe Leu Met Ile Glu Gln Asn
```

```
                    50                  55                  60
Thr Lys Ser Pro Leu Phe Met Gly Lys Val Val Asn Pro Thr Gln Lys
 65                  70                  75                  80

<210> SEQ ID NO 39
<211> LENGTH: 418
<212> TYPE: PRT
<213> ORGANISM: Homo sapiens

<400> SEQUENCE: 39

Met Pro Ser Ser Val Ser Trp Gly Ile Leu Leu Leu Ala Gly Leu Cys
  1               5                  10                  15

Cys Leu Val Pro Val Ser Leu Ala Glu Asp Pro Gln Gly Asp Ala Ala
                 20                  25                  30

Gln Lys Thr Asp Thr Ser His His Asp Gln Asp His Pro Thr Phe Asn
             35                  40                  45

Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350
```

-continued

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 40
<211> LENGTH: 1352
<212> TYPE: DNA
<213> ORGANISM: Homo sapiens

<400> SEQUENCE: 40

```
ctgggacagt gaatcgacaa tgccgtcttc tgtctcgtgg ggcatcctcc tgctggcagg      60
cctgtgctgc ctggtccctg tctccctggc tgaggatccc cagggagatg ctgcccagaa     120
gacagataca tcccaccatg atcaggatca cccaaccttc aacaagatca ccccaacct     180
ggctgagttc gccttcagcc tataccgcca gctggcacac cagtccaaca gcaccaatat     240
cttcttctcc ccagtgagca tcgctacagc ctttgcaatg ctctccctgg ggaccaaggc     300
tgacactcac gatgaaatcc tggagggcct gaatttcaac ctcacggaga ttccggaggc     360
tcagatccat gaaggcttcc aggaactcct ccgtaccctc aaccagccag acagccagct     420
ccagctgacc accggcaatg ccctgttcct cagcgagggc ctgaagctag tggataagtt     480
tttggaggat gttaaaaagt gtaccactc agaagccttc actgtcaact cggggacac      540
cgaagaggcc aagaaacaga tcaacgatta cgtggagaag ggtactcaag gaaaattgt      600
ggatttggtc aaggagcttg acagagacac agttttgct ctggtgaatt acatcttctt      660
taaaggcaaa tgggagagac cctttgaagt caaggacacc gaggaagagg acttccacgt     720
ggaccaggtg accaccgtga aggtgcctat gatgaagcgt ttaggcatgt ttaacatcca     780
gcactgtaag aagctgtcca gctgggtgct gctgatgaaa tacctgggca atgccaccgc     840
catcttcttc ctgcctgatg aggggaaact acagcacctg gaaaatgaac tcacccacga     900
tatcatcacc aagttcctgg aaaatgaaga cagaaggtct gccagcttac atttacccaa     960
actgtccatt actggaacct atgatctgaa gagcgtcctg ggtcaactgg gcatcactaa    1020
ggtcttcagc aatggggctg acctctccgg ggtcacagag gaggcacccc tgaagctctc    1080
caaggccgtg cataaggctg tgctgaccat cgacgagaaa gggactgaag ctgctggggc    1140
catgttttta gaggccatac ccatgtctat ccccccccgag gtcaagttca acaaaccctt    1200
tgtcttctta atgattgaac aaaataccaa gtctcccctc ttcatgggaa agtggtgaa     1260
tcccacccaa aaataactgc ctctcgctcc tcaacccctc cctccatcc ctggcccct      1320
ccctggatga cattaaagaa gggttgagct gg                                    1352
```

<210> SEQ ID NO 41
<211> LENGTH: 25
<212> TYPE: RNA
<213> ORGANISM: Artificial Sequence
<220> FEATURE:
<223> OTHER INFORMATION: Primer

<400> SEQUENCE: 41
cgaauccuaa ugcugcuccc uacuu                                              25

```
<210> SEQ ID NO 42
<211> LENGTH: 25
<212> TYPE: RNA
<213> ORGANISM: Artificial Sequence
<220> FEATURE:
<223> OTHER INFORMATION: Primer

<400> SEQUENCE: 42
aaguagggag gagcauuacc auucg                                          25

<210> SEQ ID NO 43
<211> LENGTH: 25
<212> TYPE: RNA
<213> ORGANISM: Artificial Sequence
<220> FEATURE:
<223> OTHER INFORMATION: Primer

<400> SEQUENCE: 43
cuuuggugcc aacucugccu cucuu                                          25

<210> SEQ ID NO 44
<211> LENGTH: 25
<212> TYPE: RNA
<213> ORGANISM: Artificial Sequence
<220> FEATURE:
<223> OTHER INFORMATION: Primer

<400> SEQUENCE: 44
aagagaggca gaguuggcac caaag                                          25
```

METHOD FOR AMELIORATING RADIATION EXPOSURE EFFECTS WITH ALPHA-1 ANTITRYPSIN

PRIORITY

This application is a National Stage application filed under Rule 371 based on PCT/US12/28568 filed Mar. 9, 2012 which claims priority to U.S. provisional patent application Ser. No. 61/452,026, filed Mar. 11, 2011, and Ser. No. 61/523,759 filed on Aug. 15, 2011, which are incorporated herein by reference in their entirety for all purposes.

FIELD

Embodiments herein relate to compositions, methods and uses for alpha-1 antitrypsin ($\alpha$-1 antitrypsin, AAT) or derivative or analog or peptide or mutant thereof for treating a subject exposed to radiation. In certain embodiments, AAT or derivative thereof or analog thereof may be used to modulate adverse effects of radiation therapy on subject undergoing treatment for cancer. In other embodiments, compositions disclosed herein can be used for treating a subject having been exposed to non-therapeutic or accidental radiation. Some embodiments reported herein concern compositions and methods for enhancing radiotherapy. Certain embodiments relate methods and compositions for preventing or reducing radiation exposure induced cellular damage in a subject.

BACKGROUND

AAT

Normal plasma concentration of alpha-1 antitrypsin (AAT) ranges from 1.3 to 3.5 mg/ml. Under certain conditions, AAT easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen.

Radiation Therapy

Radiation therapy, radiation oncology, or radiotherapy, can be used as part of cancer treatment to control malignant cells by a health professional. Radiotherapy may be used for curative or an ameliorating treatment. It can be used at times when a cure is not possible and the aim is for local disease control or symptomatic relief or as therapeutic treatment where the therapy has survival benefit and it can be curative. Total body irradiation (TBI) can be used to prepare a subject to receive a bone marrow transplant. Radiotherapy has other applications in non-malignant conditions, such as the treatment of trigeminal neuralgia, severe thyroid eye disease, pterygium, pigmented villonodular synovitis, prevention of keloid scar growth, and prevention of heterotopic ossification. Use of radiotherapy in these conditions is limited partly by concerns about the risk of radiation-induced cancers.

Radiotherapy can also be used in combination therapies with surgery, chemotherapy, hormone therapy, immunotherapy or combinations of therapies. Most cancer types can be treated with radiotherapy in some manner. The precise treatment intent can depend on the tumor type, location, and stage, as well as the general health of the patient.

Radiation Induced Cellular Damage

At high doses, radiation-induced cellular damage and lethality can be associated with hematopoietic and gastrointestinal radiation syndromes. Hematopoietic syndrome is characterized by loss of hematopoietic cells and their progenitors making it impossible to regenerate blood and lymphoid system. Death can often occur as a consequence of infection, hemorrhage and/or anemia. GI syndrome is caused by massive cell death in the intestinal epithelium, predominantly in the small intestine, followed by disintegration of intestinal wall and death from bacteriemia and sepsis. Hematopoietic syndrome usually prevails at the lower doses of radiation and leads to a more delayed death than GI syndrome.

SUMMARY

Embodiments herein provide for methods and compositions for treating a subject undergoing radiation treatment or having been exposed to radiation. In certain embodiments, compositions and methods concern modulating adverse effects of radiation on a subject in need thereof. In accordance with these embodiments, methods disclosed herein can be used to reduce or prevent cellular damage induced by radiation exposure in the subject. In some embodiments, compositions and methods concern treating a subject having radiation therapy or radiation for example, when administered to a subject having cancer or suspected of developing a malignancy or for uncontrolled cellular growth. Other embodiments disclosed herein concern treating a subject having been exposed to radiation, for example, by accident or by a purposeful act such as a nuclear accident or attack. Other embodiments concern protecting or preventing consequences of radiation exposure in a subject undergoing or having undergone a diagnostic procedure.

Compositions contemplated herein concern naturally occurring alpha-1 antitrypsin (e.g. human AAT), commercially available AAT formulations, or fragments, or derivatives thereof, or recombinants, or mutants thereof having no significant serine protease inhibitor activity, or alleles thereof (for example, there are approximately 100 naturally occurring AAT variants), or analogs thereof or fusion protein thereof (e.g. a human IgG or fragment of human IgG). Some embodiments concern administering naturally occurring AAT to a subject having been exposed to radiation or radiation damage. Other embodiments can concern administering a composition of one or more carboxyterminal derivative(s) or fragment(s) of AAT including, for example, a fragment of the last 80 AAs of the molecule to a subject. It is contemplated herein that a subject that is scheduled to undergo radiation therapy can be treated before, during or after radiation therapy. In addition, a subject having had radiation damage due to exposure can be treated even after adverse effects have occurred in order, for example, to reduce any additional adverse effects that can be a consequence of exposure relative to a control not receiving compositions disclosed herein. Treatments after radiation can be before, during, immediately after or up to several days to a month after exposure or treatment of radiation. In accordance with these embodiments, treatments disclosed herein can be use to protect normal, non-cancerous cells, from radiation exposure.

In accordance with these embodiments, an early treatment can be before (for example, before treatment), during or within 48 hours after treatment or exposure. In other embodiments, a late treatment can be one administered after 48 hours or up to days, weeks or months after treatment or exposure depending on the subject and the circumstances surrounding treatment or exposure. In yet other embodiments, compositions disclosed herein can be used to treat a subject undergoing cancer treatments using radiation therapy, to modulate adverse effects and normal cell damage and dysfunction as a consequence of the radiation exposure by about 5%, or about 10%, or about 15%, or about 20% or about 25%, or about 30% or more compared to a subject not treated with these compositions.

In other embodiments, compositions disclosed herein can be used to modulate production of enzymes or activity of pathways induced by radiation exposure. In certain embodiments, compositions administered to a subject having such an exposure or treatment can modulate cellular damage in the subject. In some embodiments, compositions described herein can be used for inhibiting radiation induced inflammatory molecules.

Compositions contemplated herein may further include an agent selected from the group consisting of an anti-inflammatory agent, an immunosuppressive agent, an immunomodulatory agent, an anti-viral agent, an anti-pathogenic agent, an anti-bacterial agent, a protease inhibitor, and a combination thereof. Any agent of use to treat a subject having radiation therapy or exposed to radiation can be combined with compositions disclosed herein for ameliorating cellular damage, or other side effects or symptoms related to such an exposure.

In certain embodiments, compositions for administration can be in a range of between about 10 ng and about 10 mg per ml or mg of the formulation. A therapeutically effective amount of AAT peptides or drugs that have similar activities as AAT or peptides drug may be measured in molar concentrations and may range between about 1 nM and about 10 mM with treatments of about 1 mg/kg to about 110 mg/kg per dose. The compositions disclosed herein are also contemplated to be administered in combination with a pharmaceutically acceptable carrier or excipient. Accurate doses for a subject can be established by well known routine clinical trials without undue experimentation. In one embodiment, a subject may be treated for radiation therapy exposure or radiation exposure with a single dose (e.g about 40 mg/kg to about 80 mg/kg) of an active agent (e.g. AAT or fragment thereof or mutant thereof or recombinant molecule thereof). In accordance with these embodiments, the subject can be treated with follow-on treatments (e.g. daily or 5 to 10 days following a single dose) as determined by a health professional. Other embodiments can include using a control population having a placebo (e.g. human serum albumin administration or other comparable placebo) and comparing a placebo effect to a population receiving compositions disclosed herein. In some embodiments, compositions disclosed herein can range from about 1 to about 150 mg/kg in single, twice daily, daily or in multiple doses to a subject. In other embodiments, a composition disclosed herein can be administered to a subject every time a subject undergoes radiation.

Some embodiments disclosed herein concern treatment of a subject undergoing cancer therapies. Cancer therapies can include, but are not limited to, treatment for bladder, breast, brain, kidney, leukemia, lung, myeloma, liposarcoma, lymphoma, tongue, prostate, stomach, colon, uterine cancers, melanoma, pancreatic, eye and other known cancers.

In certain embodiments, radiation therapy can be associated with a wide variety of side effects which depend on the dose of radiation administered and the tissues exposed. Side effects can include, but are not limited to, acute inflammation associated with effects such as cellular damage, pain, swelling and local irritation and chronic effects such as fibrosis, scaring, and loss of tissue integrity with changes such as increased tissue friability and bleeding. Acute effects can depend on the type of organ or tissue irradiated. For example, head and neck irradiation can be associated with pain, difficulty in swallowing and affects on maintaining nutrition.

Bowel irradiation can be associated with severe cellular damage, pain, diarrhea, and intestinal bleeding. Prostate irradiation can result in bowel and bladder irritation. Chronic side effects of radiation of the bowel can include fibrosis and obstruction. Irradiation of the prostate can be associated with chronic incontinence and erectile dysfunction. Irradiation of the lung can be associated in intense fibrosis of the affected lung with loss of normal lung function. Whole body irradiation or radiation of the bone marrow can result in both acute and chronic immunodeficiency, opportunistic infections and death.

Some embodiments disclosed herein concern treating a subject having prostate cancer. In accordance with these embodiments, a male subject having prostate cancer can be treated with compositions disclosed herein before, during or after radiation therapy in order to reduce development of impotence or erectile dysfunction, common side effects of prostate cancer therapies. It is contemplated that a male subject undergoing such a treatment (e.g. AAT composition administration) can be monitored for penile function and dose regimen can be adjusted by a healthcare professional based on individual needs at the time.

In certain embodiments, the subject is a mammal. In some embodiments, the mammal is a human. In yet other embodiments, the subject is a pregnant female or young child. In other embodiments, the subject is a pet, a domesticated animal or livestock.

In other embodiments, the subject or mammal can be a non-domesticated mammal such as a captive or free wild animal.

In certain embodiments, synthetic and/or naturally occurring peptides may be used in compositions and methods herein for example, providing other than the serine protease inhibitor activity of AAT. Homologues, natural peptides derivatives, with sequence homologies to AAT including peptides directly derived from cleavage of AAT may be used or other peptides such as, peptides that have AAT-like activity other than serine protease inhibitor activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances can include, but are not limited to, certain phenylenedialkanoate esters, CE-2072, UT-77, and triazole peptoids. Examples of analogues are TLCK (tosyl-L-lysine chloromethyl ketone) or TPCK (tosyl-L-phenylalanine chloromethyl ketone) or any combination thereof.

In certain embodiments, compositions comprising human AAT mutants can be generated having no significant serine protease inhibitor activity of use in methods described herein (e.g AAT peptide derivative, AAT recombinant or AAT mutant). In other embodiments, constructs of human AAT mutants having no significant serine protease activity can be associated with a vector. Other embodiments concern AAT-derived fragment constructs adapted to have no significant serine protease inhibitor activity.

Other embodiments concern combination therapies for the treatment of a subject undergoing cancer related therapies, for example a composition disclosed herein can be combined with any other agent known to shrink or eliminate a tumor or reduce metastasis of a tumor in the subject or treat other aspects of cancer in the subject.

In some embodiments, AAT peptides contemplated for use in the compositions and methods of the present invention are also intended to include any and all of those specific AAT peptides including, but not limited to, 5 or 10 amino acid AAT derived peptides of SEQ ID NO:1 or SEQ ID NO:39. Any combination of consecutive amino acids depicting a portion of the carboxy terminus of AAT, such as consecutive amino acid sequences derived from SEQ ID NO:1. In addition, AAT variants are contemplated of use herein. A composition herein can include, but is not limited to a carboxy-terminal peptide or amino-terminal peptides corresponding to AAT, an analog thereof, any derivative of AAT carboxy terminus that binds to serpin-enzyme complex (SEC) receptor or a combination thereof.

In certain embodiments, treating the subject with a composition encompassed herein to modulate normal cell damage can be by at least 10%, or by at least 20% or by at least 30%, or by at least 40%, or by at least 50%, or by at least 60%, or by at least 70%, or by at least 80%, or by at least 90% compared to a subject not treated with the composition.

Other embodiments herein include treating a subject undergoing radiation therapy by identifying a subject having cancer; administering a therapeutically effective amount of a composition comprising AAT, AAT derivative having no significant serine protease inhibitor activity, AAT-like compound, AAT analog, AAT derivative, one or more peptides derived from AAT, any derivative or fragment of AAT carboxy terminus having no significant serine protease inhibitor activity or combination thereof to the subject before, during and/or after radiation therapy and assessing radioprotection by the composition. Administering the composition can include administering the composition directly to the tumor (e.g. lung, kidney, pancreas, bone, skin) or other delivery methods such as intravenously or subcutaneously, inhalation or via a catheter. It is contemplated herein that any known delivery device of use to treat a subject having been exposed to excess radiation or undergoing radiation therapy can be used in any embodiment provided.

As such, those skilled in the art will appreciate that the concepts, upon which this disclosure is based, can readily be used as a basis for designing other methods for carrying out the several features and advantages of embodiments of the present invention.

BRIEF DESCRIPTIONS OF THE DRAWINGS

The foregoing aspects and many of the attendant advantages of this invention will become more readily appreciated as the same become better understood by reference to the following detailed description, when taken in conjunction with the accompanying drawings, wherein.

Figure 3:
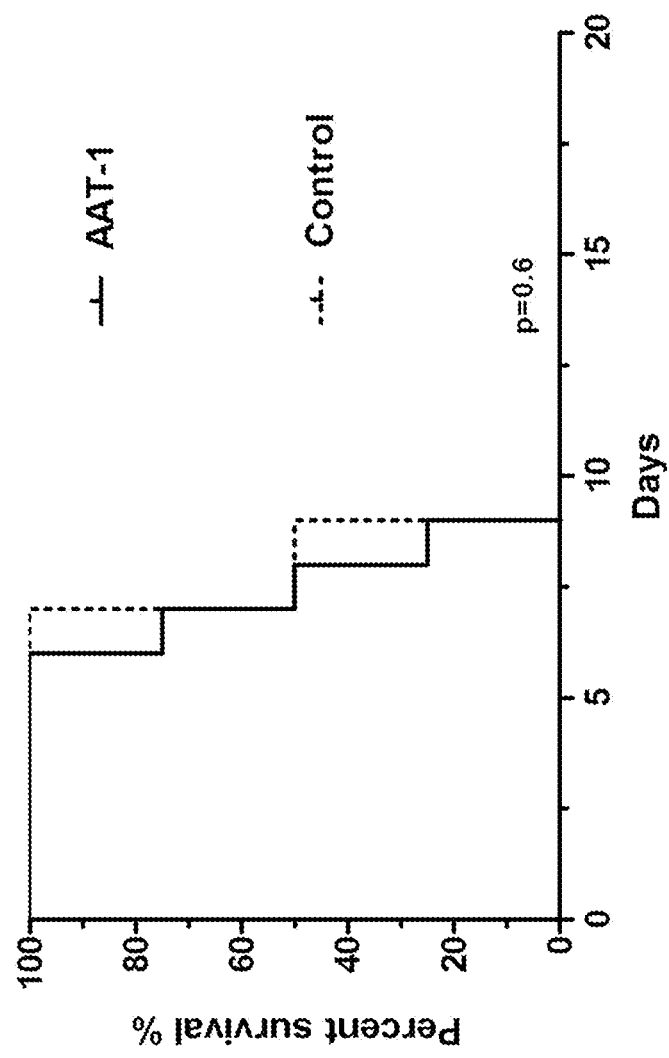

FIG. 3 represents an exemplary graphic illustration of percent survival of mice in an experiment in which mice (n=4) were treated with 3 mg/animal AAT only after the irradiation (24 hours post exposure) with subsequent doses of 3 mg/animal of AAT every 48 hours thereafter for 10 days, as described in Example 1.

Figure 4:
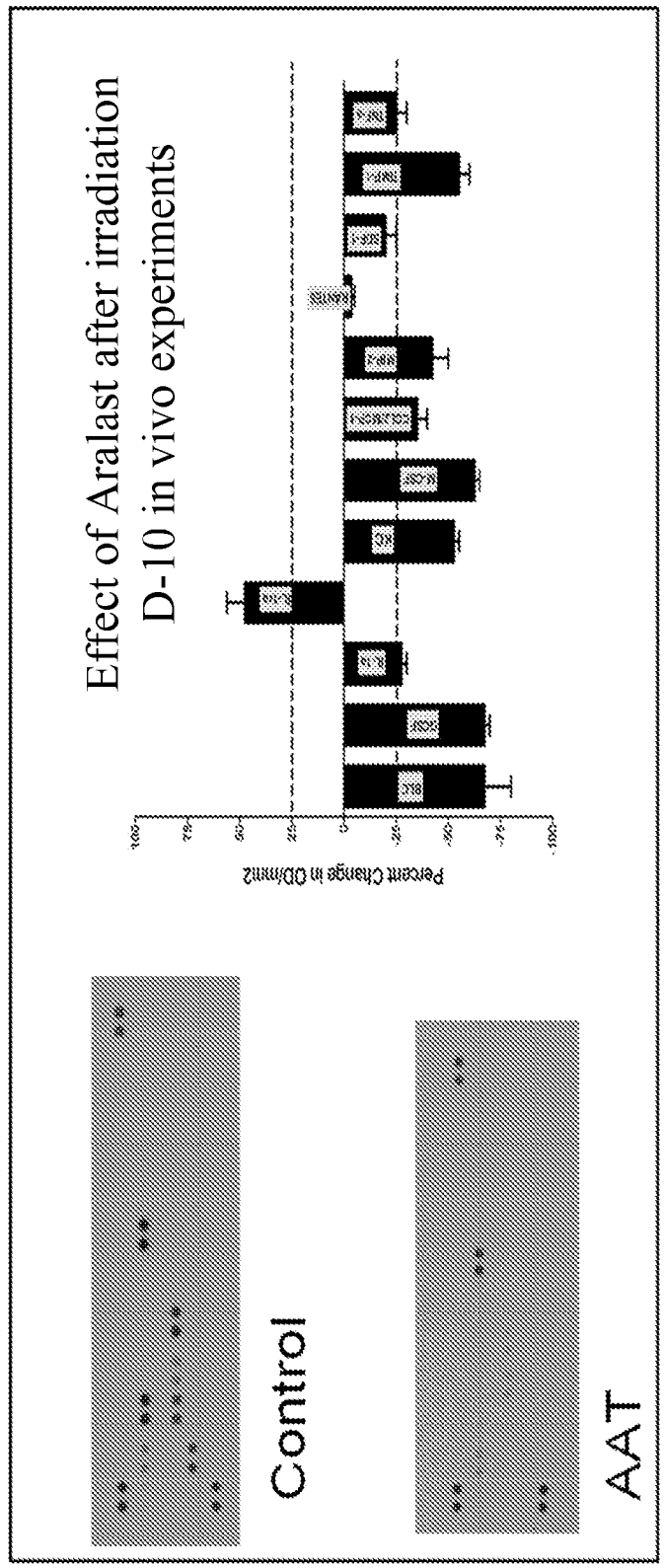

FIG. 4 represents an exemplary graphic illustration of protein levels of various cytokines assayed in serum obtained from the mice treated with AAT before and after exposure to radiation, and the control mice, as described in Example 1.

Figure 5A:
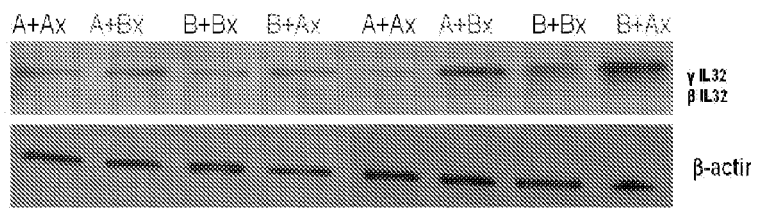

FIG. 5A represents an exemplary Western blot of unsorted PBMC (peripheral blood mononuclear cell) responder cells or sorted CD8+ responder cells isolated from allogeneic MLC (mixed-leukocyte culture) cultures illustrating relative protein levels of γIL-32, βIL-32, and the β-actin control, wherein the "x" symbol refers to irradiated cells, and "A" refers to donor A, and "B" refers to donor B, as described in Example 2.

Figure 5B:
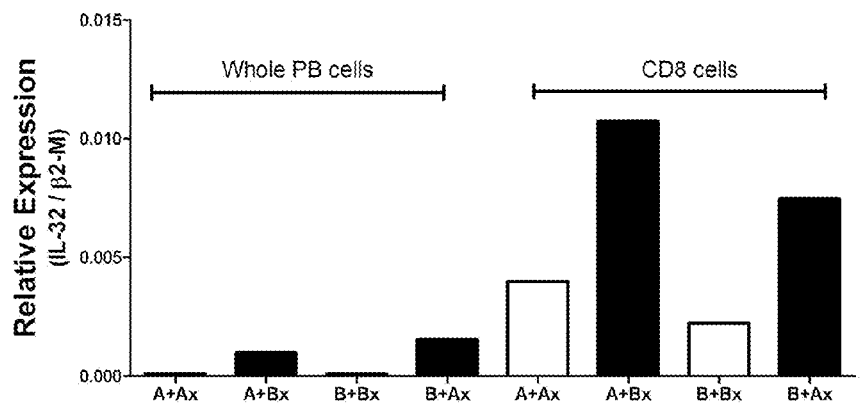

FIG. 5B represents an exemplary graph illustrating IL-32 mRNA levels in allogeneic MLC. Error bars represent mean±SEM of 3 similar experiments. Solid columns represent results in allogeneic cultures, open columns represent results in autologous controls. The results are displayed as ±SEM from 3 similar experiments. * indicates p<0.01 (Student t test), as described in Example 2.

Figure 5C:
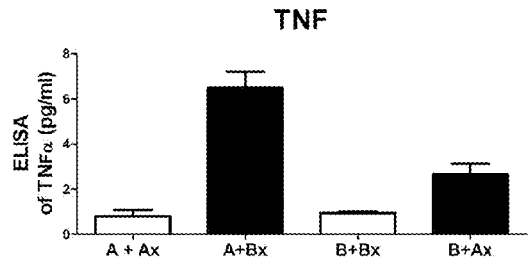

FIG. 5C represents an exemplary graph illustrating protein levels of TNFα in allogeneic MLC as determined by ELISA assay. Error bars represent mean±SEM of 3 similar experiments. Solid columns represent results in allogeneic cultures, open columns represent results in autologous controls, as described in Example 2.

Figure 5D:
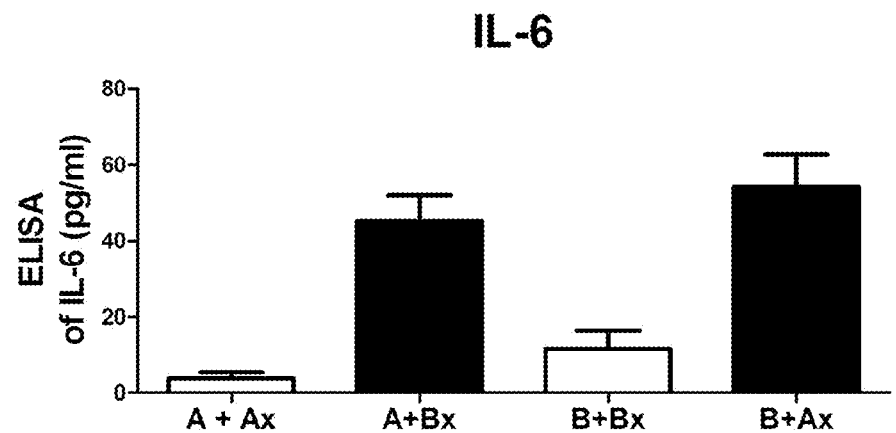

FIG. 5D represents an exemplary graph illustrating protein levels of IL-6 in allogeneic MLC as determined by ELISA assay. Error bars represent mean±SEM of 3 similar experiments. Solid columns represent results in allogeneic cultures, open columns represent results in autologous controls, as described in Example 2.

Figure 5E:
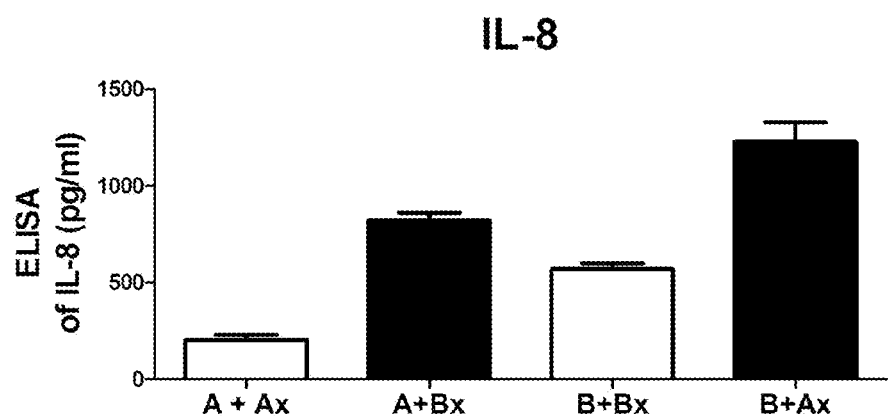

FIG. 5E represents an exemplary graph illustrating protein levels of IL-8 in allogeneic MLC as determined by ELISA assay. Error bars represent mean±SEM of 3 similar experiments. Solid columns represent results in allogeneic cultures, open columns represent results in autologous controls, as described in Example 2.

Figure 6A:
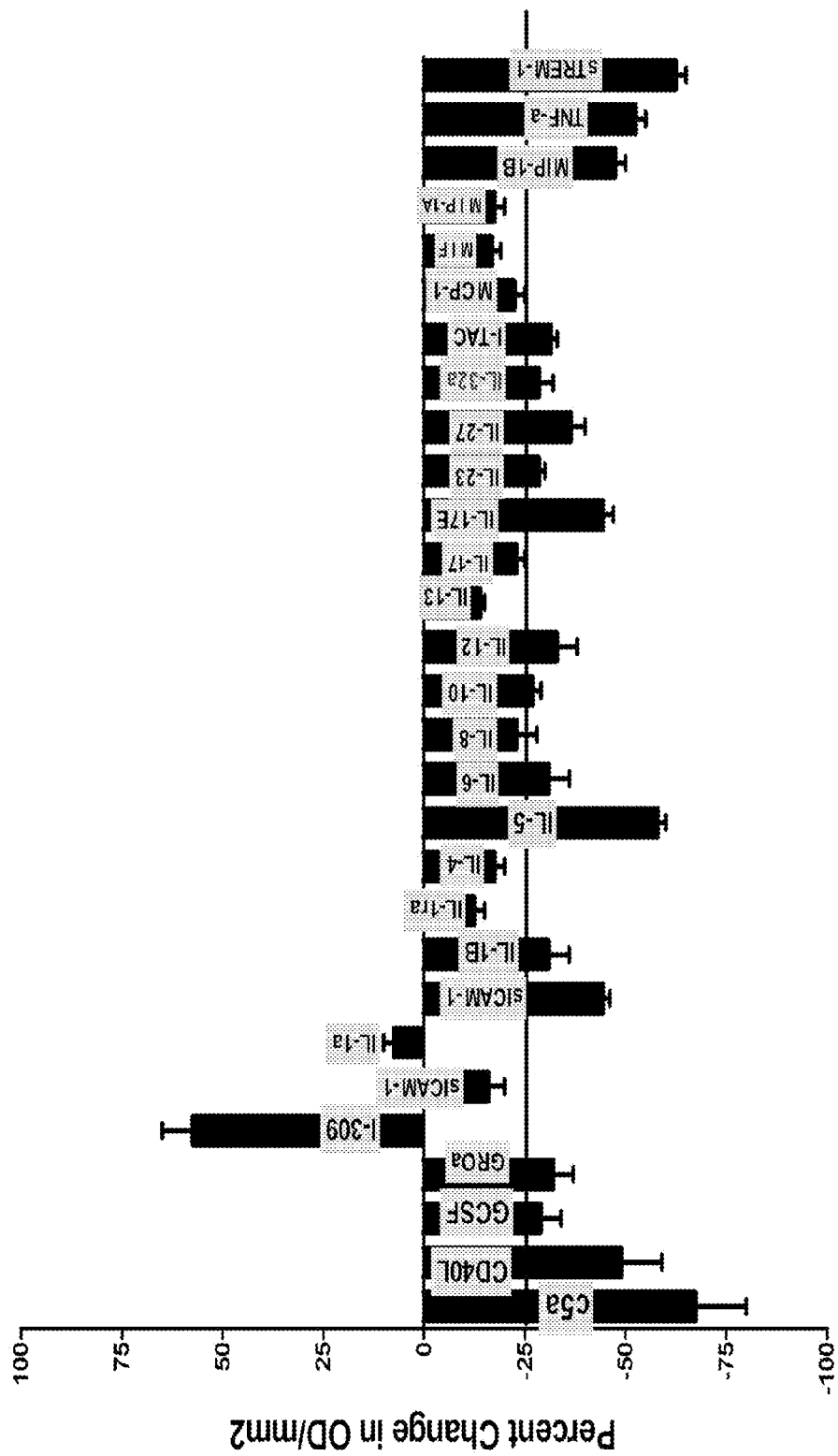

FIG. 6A represents an exemplary graph illustrating protein levels of various cytokines expressed in PBMC transfected with IL-32 specific or scrambled siRNA (control), expressed as percent change in comparison to control supernatants, as described in Example 2.

Figure 6B:
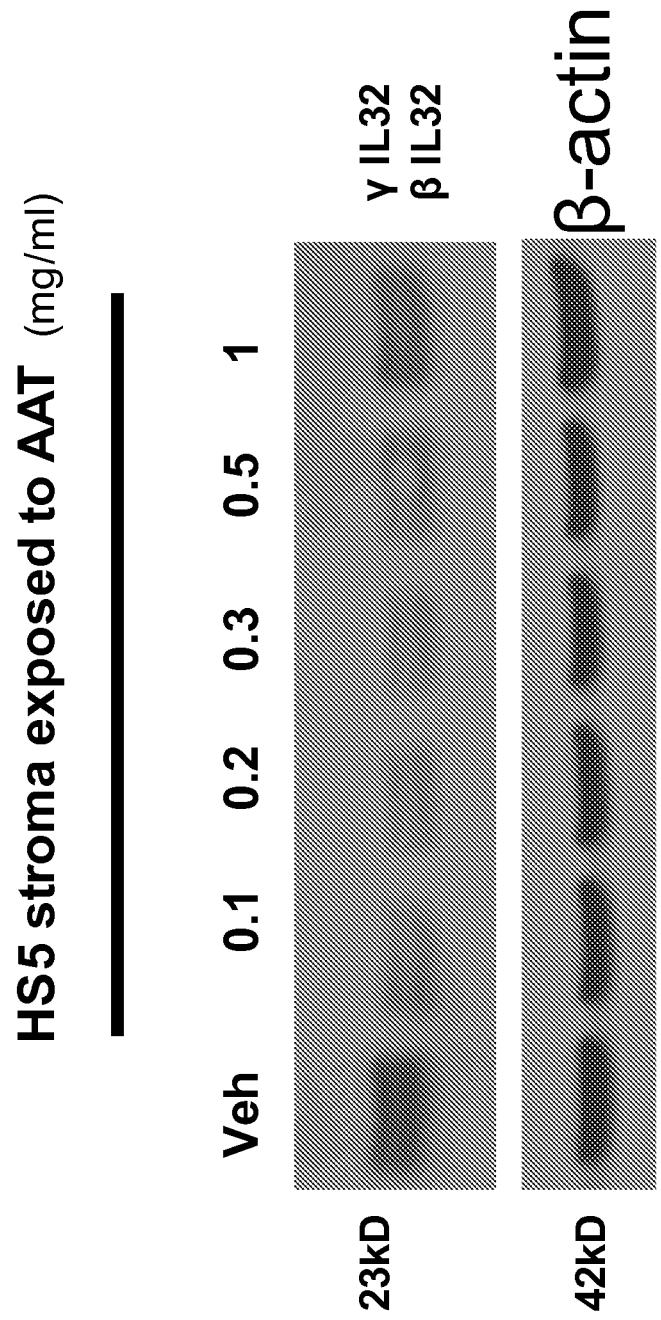

FIG. 6B represents an exemplary Western blot of protein extract of the human stroma cell line HS5 exposed to vehicle only (veh, control) or various concentrations of AAT (in serum-free medium). Illustrated are levels of IL-32 β and γ isoforms at concentrations of ATT between 0.1 and 1 mg/ml. This blot is representative of experiments, as described in Example 2.

Figure 7A:
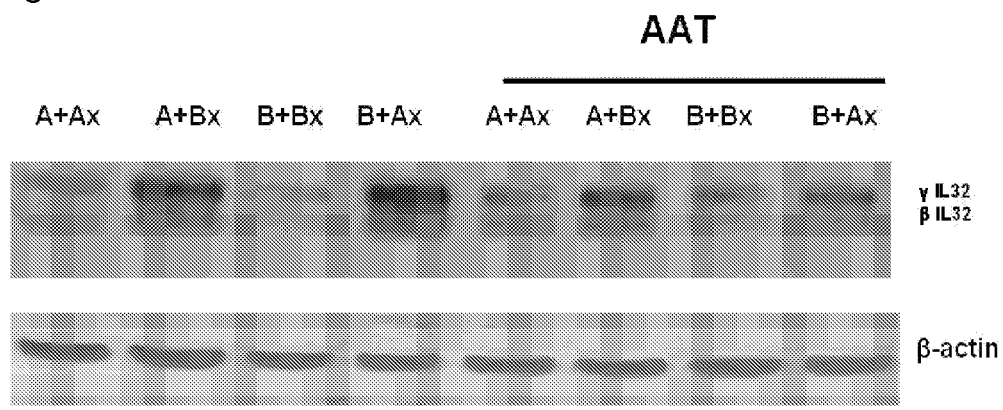

FIG. 7A represents an exemplary Western blot of IL-32β and γ levels in CD8+ cells from 7-day MLCs under control conditions and in the presence of AAT (0.3 mg/ml) and IL-32 β and γ isoforms in the presence of AAT. The Western blot is representative of similar experiments, as described in Example 2.

Figure 7B:
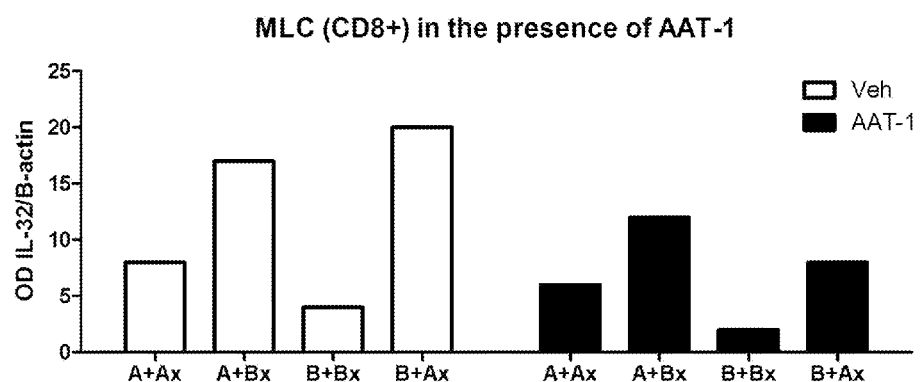

FIG. 7B represents an exemplary graph illustrating expression changes in IL-32 protein levels in allogeneic MLCs and autologous controls as determined by densitometry (OD) of the same biological experiment. Open columns reflect results in the absence of AAT; solid columns in the presence of AAT, as described in Example 2.

Figure 7C:
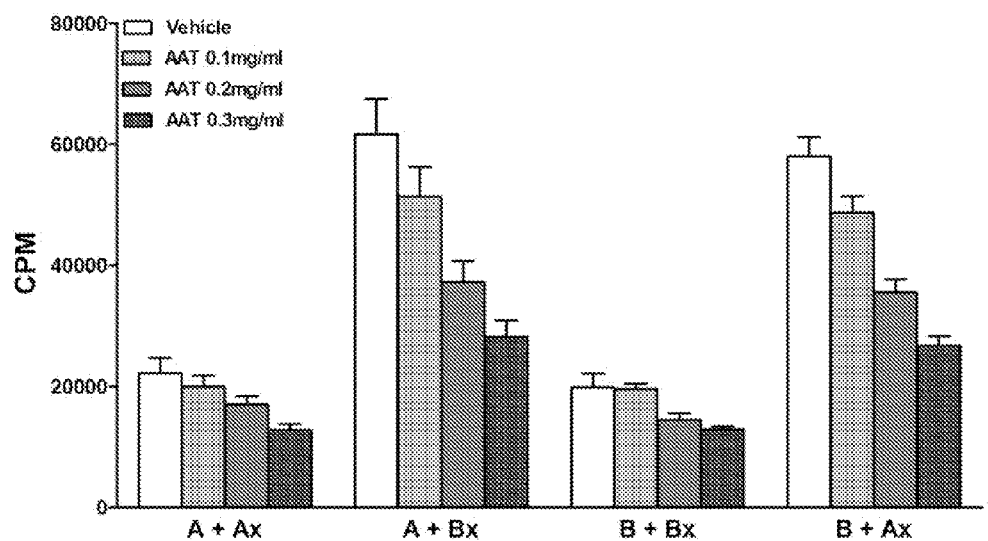

FIG. 7C represents an exemplary graph illustrating proliferation in MLC (as measured by $^3$H thymidine uptake; CPM, mean±SEM), as described in Example 2.

Figure 7D:
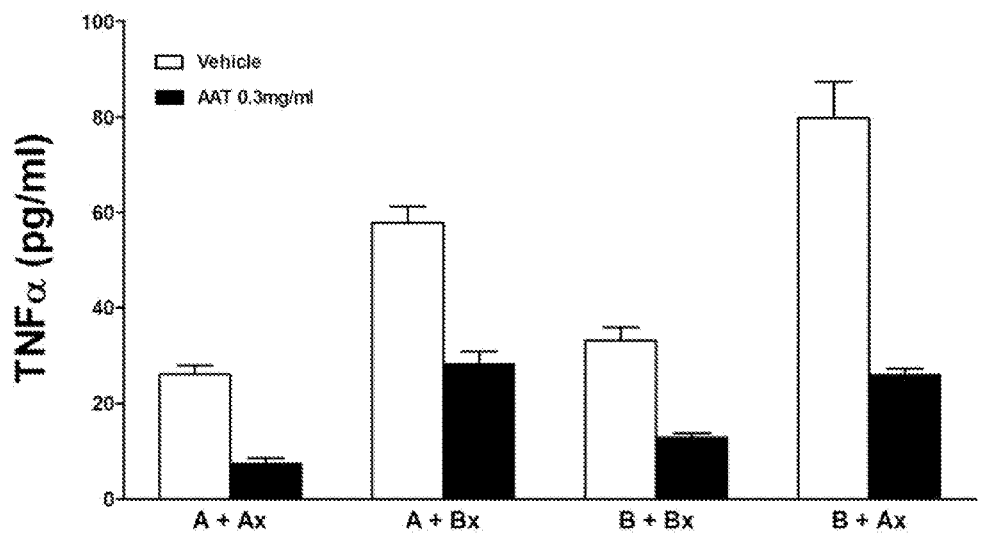

FIG. 7D represents an exemplary graph illustrating results of a TNF-α ELISA assay measuring the secretion of TNF a in the presence and absence of AAT. * indicates p<0.05 (Student t test), as described in Example 2.

Figure 8A:
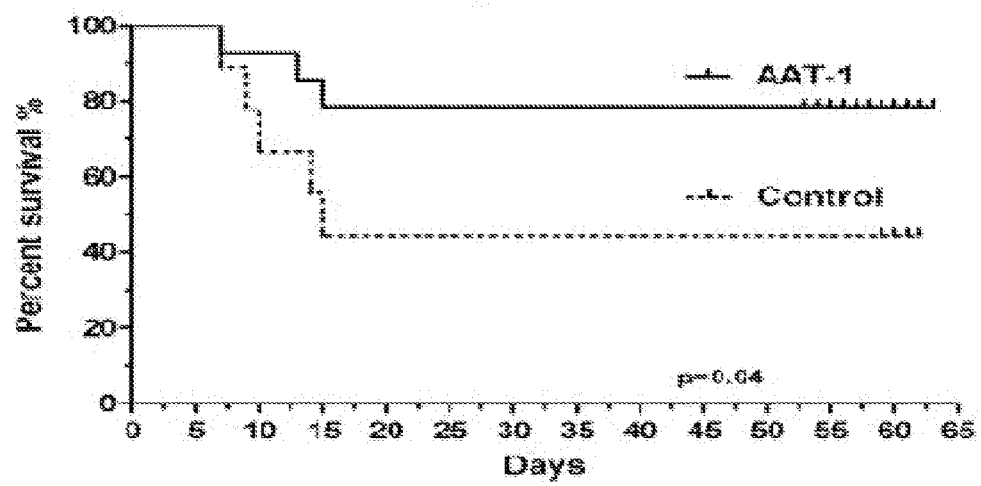

FIG. 8A represents an exemplary graph illustrating percent survival of AAT-treated mice versus albumin-treated control mice (n=15 for each group, 0.04). As shown in FIG. 8A, by day 65 after transplantation survival was 80% in AAT-treated mice versus 40% in albumin treated controls (n=15; p=0.04, log rank), as described in Example 3.

Figure 8B:
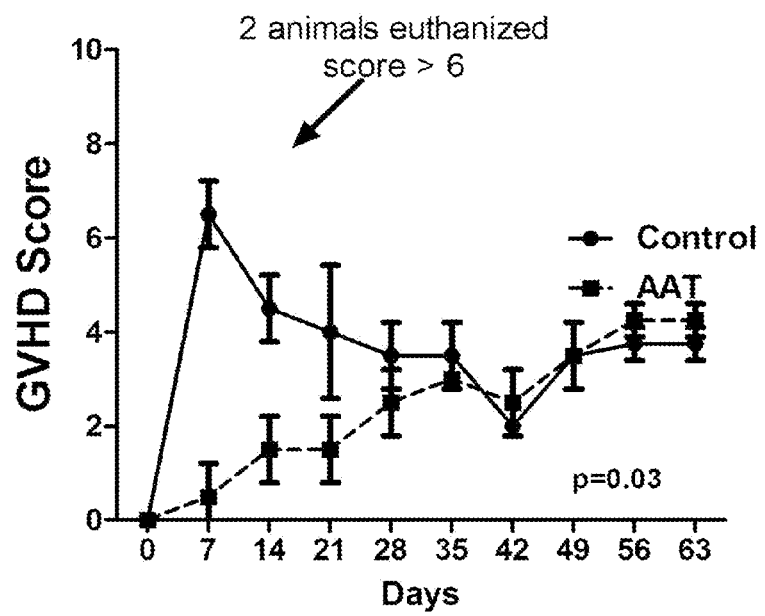
Figure 8C:
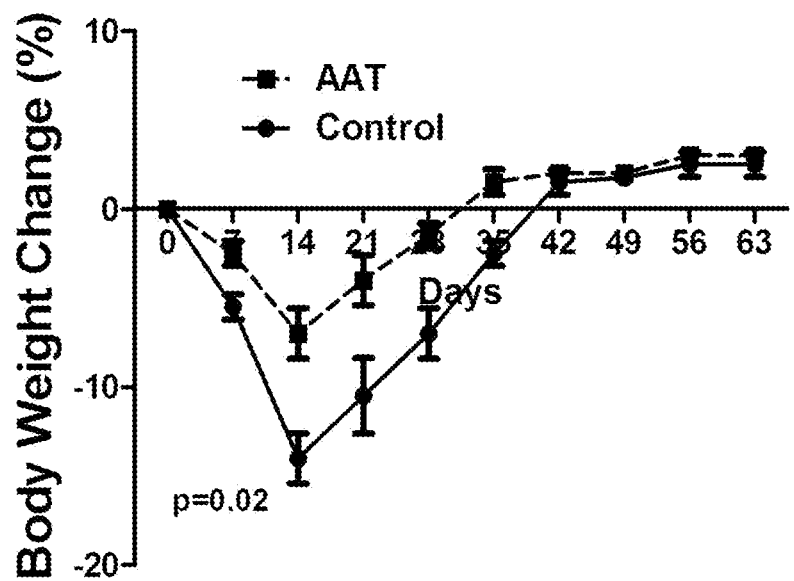
Figure 8D:
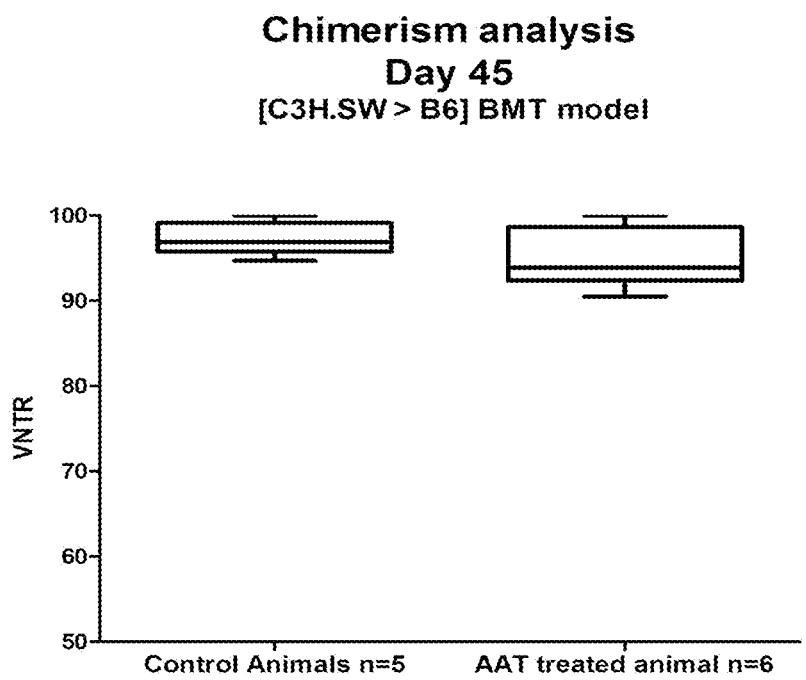

FIG. 8B represents an exemplary graph illustrating severity of GVHD in the AAT-treated mice versus the albumin-treated control mice, as described in Example 3;

FIG. 8C represents an exemplary graph illustrating change in body weight of transplanted AAT-treated mice and albumin-treated mice over time post-transplant (mean±SEM; n=15), as described in Example 3;

FIG. 8D represents an exemplary graph illustrating proportion of donor cells among PBMC in AAT-treated (n=6) versus albumin-treated (n=5) mice at day 45 (p=0.25), as described in Example 3.

Figure 9A:
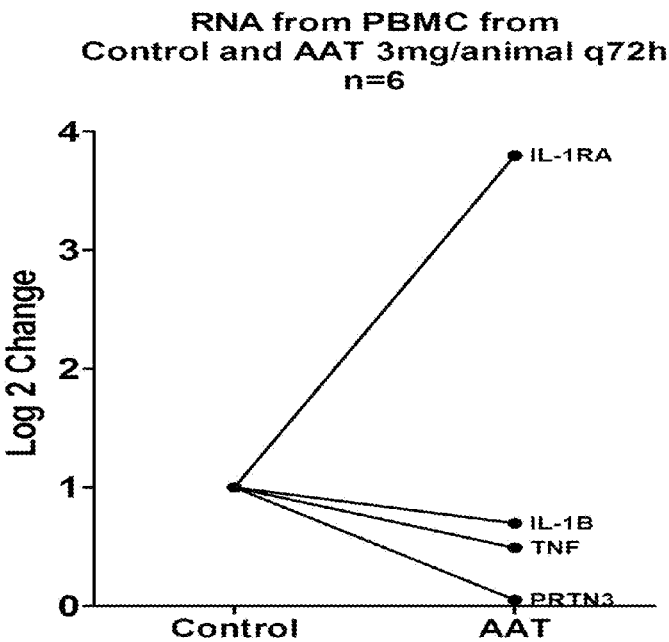

FIG. 9A represents an exemplary graph illustrating the log 2 change in RNA levels of IL-1Ra, IL-1β, TNF-α, and PR3 ire PBMC, as determined by RT-PCR. Changes in cytokine concentration are expressed as percent change compared to albumin control. The horizontal dotted line indicates an increase/decrease of 25% as described in Example 3.

Figure 9B:
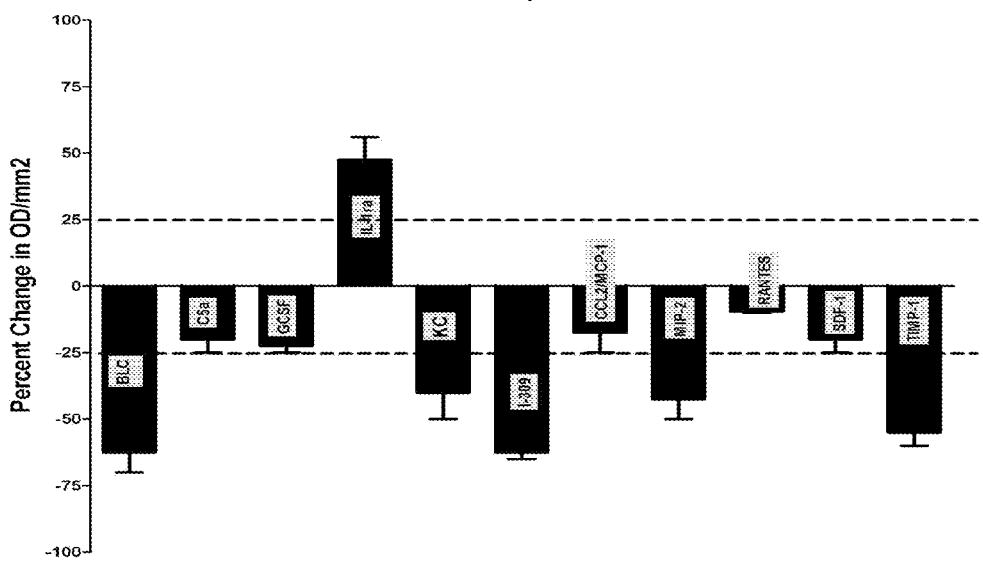

FIG. 9B represents an exemplary graph illustrating mean±SEM cytokine plasma levels at 3 days after transplantation as described in Example 3.

Figure 9C:
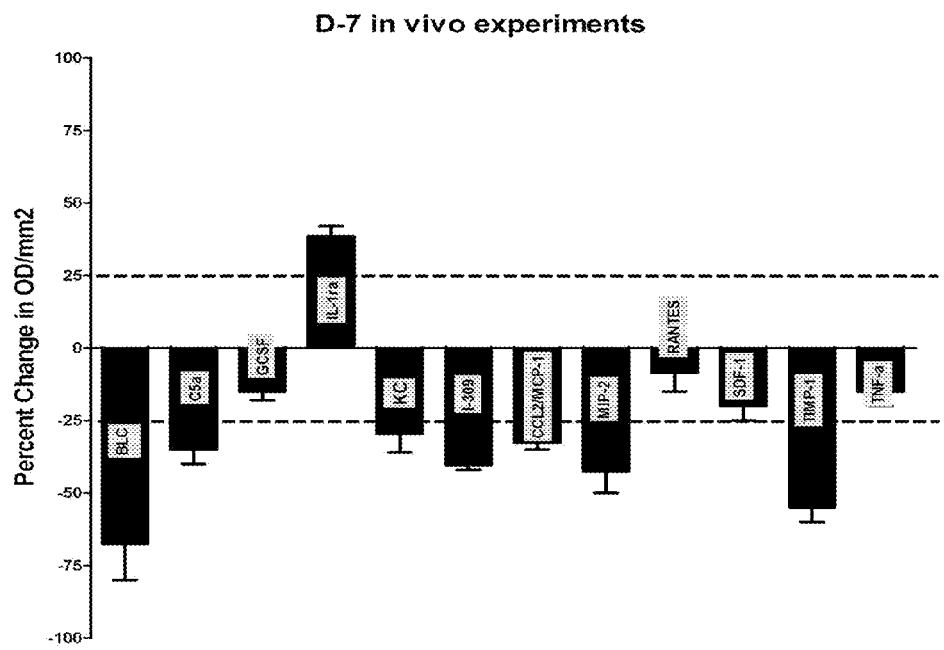

FIG. 9C represents an exemplary graph illustrating mean±SEM cytokine plasma levels at 7 days after transplantation as described in Example 3.

Figure 9D:
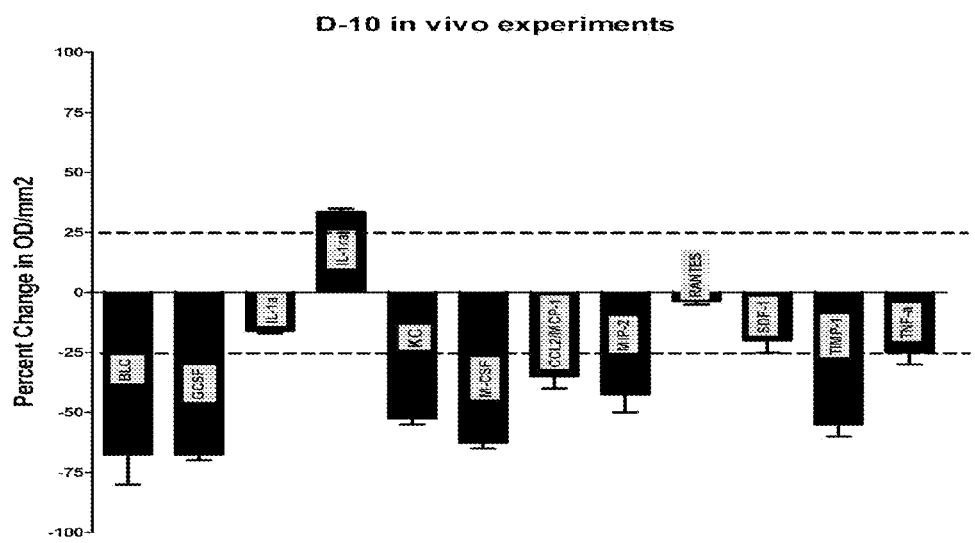

FIG. 9D represents an exemplary graph illustrating mean±SEM cytokine plasma levels at 10 days after transplantation as described in Example 3.

DESCRIPTION OF ILLUSTRATIVE EMBODIMENTS

Definitions

As used herein, "a" or "an" may mean one or more than one of an item.

As used herein, "about" can mean plus or minus 10%, for example, about 10 minutes can mean from 9 to 11 minutes.

As used herein, the term "effective amount" of a composition or agent refers to a quantity of composition or agent sufficient to achieve a desired effect in a subject being treated. An effective amount of a compound can be administered in a single dose or in several doses (daily, for example) during a course of treatment. However, the effective amount of the compound will be dependent on the compound applied, the subject being treated, the severity and type of the affliction, and the manner of administration of the compound.

As used herein, the term "preventing" can refer to inhibiting to the full extent development of something (such as a disease, damage, a condition, etc.), for example, inhibiting the development of cellular or tissue damage after radiation therapy or other exposure to energetic radiation.

As used herein, the term "treating or treatment" refers to a therapeutic intervention that ameliorates a sign or symptom after it has begun to develop.

As used herein, the term "Radioprotectant or Radioprotection" can refer to a cytoprotective substance, such as compositions disclosed herein (e.g. AAT) that prevents or lessens damaging effect(s) of radiation, particularly on cells, biological tissues, organs, or organisms. Radioprotectants can permit cells and tissues to survive, and optimally heal and grow, in spite of radiation damage. Radioprotectants reduce, minimize or block the ability of radiation injury to drive cell death. Cell death and tissue damage can be measured by many methods known art methods. Any of these methods are contemplated herein.

As used herein, the term "radiation" can refer to energy in the form of waves or moving subatomic particles emitted by an atom or other body as it changes from a higher energy state to a lower energy state. Common sources of radiation include radon gas, cosmic rays from outer space, and medical X-rays. Radiation can be classified as ionizing or non-ionizing radiation, depending on its effect on atomic matter. The most common use of the word "radiation" refers to ionizing radiation. Ionizing radiation has sufficient energy to ionize atoms or molecules, while non-ionizing radiation does not. Radioactive material is a physical material that emits ionizing radiation. There are three common types of radiation: alpha, beta, and gamma radiation. They are all emitted from the nucleus of an unstable atom. X rays produced by diagnostic and metallurgical imaging and security screening equipment are also ionizing radiation, as are neutrons produced by nuclear power generation and nuclear weapons. Sources of radiation exposure include, but are not limited to, radiotherapy, nuclear warfare, nuclear reactor accidents, and improper handling of research or medical radioactive materials.

As used herein, the term "Radiation Dosage" refers to the rad is a unit of absorbed radiation dose defined in terms of the energy actually deposited in the tissue. One rad is an absorbed dose of 0.01 joules of energy per kilogram of tissue. The more recent SI unit is the gray (Gy), which is defined as 1 joule of deposited energy per kilogram of tissue. Thus, one gray is equal to 100 rad. To accurately assess the risk of radiation, the absorbed dose energy in rad is multiplied by the relative biological effectiveness (RBE) of the radiation to get the biological dose equivalent in rems. Rem stands for "Rontgen Equivalent Man". In SI units, the absorbed dose energy in grays is multiplied by the same RBE to get a biological dose equivalent in sieverts (Sv). The sievert is equal to 100 rem.

As used herein, the term "Radiation Poisoning," also called radiation sickness or acute radiation syndrome, can refer to damage to biological tissue due to excessive exposure to ionizing radiation. The term is generally used to refer to acute problems caused by a large dosage of radiation in a short period, though this also has occurred with long term exposure to low level radiation. Many of the symptoms of radiation poisoning result from ionizing radiation interference with cell division. Beneficially, this same interference enables treatment of cancer cells; such cells are among the fastest-dividing in the body, and in certain instances can be destroyed by a radiation dose that adjacent normal cells are likely to survive. Symptoms of radiation poisoning include: reduction of red and/or white blood cell count, decreased immune function (with increased susceptibility to infection), nausea and vomiting, fatigue, sterility, hair loss, tissue burns and necrosis, gastrointestinal damage accompanied by internal bleeding, and so forth.

As used herein, the term "Radiation Therapy (Radiotherapy)" refers to the treatment of disease (e.g., cancer or another hyperproliferative disease or condition) by exposure of a subject or his/her tissue to a radioactive substance. Radiotherapy may be used for curative or adjuvant cancer treatment. It is used as palliative treatment where cure is not possible and the aim is for local disease control or symptomatic relief of the subject.

As used herein, the term "cancer" can mean uncontrolled cellular growth, malignant growth or metastatic growth or tumor caused by abnormal and uncontrolled cell division or cellular infiltration or invasion where it can spread to other parts of the body through the lymphatic system or the blood stream.

As used herein, the term "cancer treatment" can mean any treatment for cancer known in the art including, but not limited to, chemotherapy and radiation therapy.

As used herein, the term "derivative", when used in the context of a peptide or polypeptide, can mean a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the invention. Other derivatives include, but are not limited to, polypeptides having a covalently modified N- or C-terminus, PEGylated peptides or polypeptides, peptides or polypeptides associated with lipid moieties, alkylated peptides or polypeptides, peptides or polypeptides linked via an amino acid side chain functional group to other peptides, polypeptides or chemicals, and additional modifications as would be understood in the art.

As used herein, the term "fragment", when used in the context of a peptide or polypeptide, can mean a part, segment or portion of a reference peptide or polypeptide.

As used herein, the term "homolog", when used in the context of a peptide or polypeptide, can mean a peptide or polypeptide sharing a common evolutionary ancestor.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

DETAILED DESCRIPTION

In the following sections, various exemplary compositions and methods are described in order to detail various embodiments of the invention. It will be obvious to one skilled in the art that practicing the various embodiments does not require the employment of all or even some of the details outlined herein, but rather that concentrations, times and other details may be modified through routine experimentation. In some cases, well known methods, or components have not been included in the description.

Radiation therapy, radiation oncology, or radiotherapy, can be used as part of cancer treatment to control malignant cell growth and/or cellular expansion or abnormal cell growth by a health professional. Radiotherapy may be used for curative or an ameliorating treatment to reduce tumor size or inhibit metastasis. Radiation therapy can be used at times when a cure is not possible and the aim is for local disease control or symptomatic relief or as therapeutic treatment or in combination with surgery and where the therapy has survival benefits. For example, total body irradiation (TBI) can be used to prepare a subject to receive a bone marrow transplant in order to prepare a subject to receive bone marrow cells.

Radiotherapy has additional applications in non-malignant conditions, including, but not limited to, treatment of trigeminal neuralgia, severe thyroid eye disease, pterygium, pigmented villonodular synovitis, prevention of keloid scar growth, and prevention of heterotopic ossification. It is contemplated that compositions disclosed herein can be used in combination with therapies for cancers as well as for non-cancerous treatments that utilize radiation therapy.

Radiotherapy can be used for the treatment of malignant or targeted therapy for non-malignant cancer (e.g. brain tumor directed therapies etc). It can also be used in combination with other therapies such as surgery, chemotherapy, hormone therapy, immunotherapy or combinations of therapies. Common cancer types can be treated with radiotherapy in some manner. The precise treatment intent can depend on the tumor type, location, and stage, as well as the general health of the patient.

Some embodiments disclosed herein concern treatment of a subject undergoing cancer therapies. Cancer treatments include, but are not limited to, treatment for bladder, breast, kidney, leukemia, skin, lung, myeloma, liposarcoma, lymphoma, tongue, prostate, stomach, colon, uterine cancers, melanoma, brain, pancreatic, eye and any other known cancers. In accordance with these embodiments, radiation and/or chemotherapy treatment of a subject for cancer can be accompanied by treatment with a composition disclosed herein. In certain embodiments, radiation-induced or chemotherapy-induced damage or side effect, such as tissue necrosis and bone marrow failure following radiation or chemotherapy exposure can be reduced and/or prevented by treatment with AAT.

Chemotherapeutic agents contemplated of use for treating a condition (e.g. cancer or uncontrolled cell growth) can include, but are not limited to, actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, valrubicin, vinblastine, vincristine, vindesine, and vinorelbine and any other chemotherapeutic agent known in the art.

In another aspect, embodiments disclosed herein provide for method of preventing and treating radiation-induced necrosis and mucosal injury. In certain embodiments, administration of AAT can be used to protect a subject from radiation-induced mucosal injury. This protection can lead to decreased mortality, improved clinical parameters, and decreased histopathological evidence of necrosis in a subject receiving such a treatment. Further, embodiments disclosed herein can relate to modulation of cellular activities, such as modulation of macrophage activity in a treated subject. Other embodiments relate to inhibitory compounds including, but not limited to, naturally occurring and man-made or synthetic inhibitors of serine protease or other AAT-related activities.

In certain embodiments, compositions disclosed herein can be demonstrated as affecting cytokine levels. For IL-32 levels showed suppression of IL-32 and T-lymphocyte proliferation. These findings suggest that AAT modulates immune and inflammatory functions and represents a novel approach to reduce or prevent cellular damage induced by radiation exposure in a subject in need thereof, either in the context of radiation therapy or other radiation exposure, and may also be used to prevent graft versus host disease (GVHD).

Injury and death of normal cells from ionizing radiation can occur as a combination of direct radiation-induced damage to exposed cells or tissues and an active genetically programmed cell reaction to radiation-induced stress resulting in cellular death. Exposure to ionizing radiation (IR) may be short or long term, it may be applied as a single or multiple doses, to the whole body, site-directed or locally. During nuclear accidents or attacks exposure may include a single high dose of whole body irradiation (sometimes followed by a long-term poisoning with radioactive isotopes). This can be true (with strict control of the applied dose) for pretreatment of patients for example for bone marrow transplantation when it is necessary to prepare hematopoietic organs for a donor's bone marrow by "cleaning" them from the host blood precursors. Cancer treatment may involve multiple doses of local irradiation that greatly exceeds lethal dose if it were applied as a total body irradiation. Poisoning or treatment with radioactive isotopes can result in long-term local exposure to radiation of targeted organs (e.g., thyroid gland in the case of inhalation of 125I). Finally, there are many physical forms of ionizing radiation differing significantly in the severity of biological effects.

At the molecular and cellular level, radiation particles can produce breakage and cross-linking in the DNA, proteins, cell membranes, and other macromolecular structures. Ionizing radiation can also induce secondary damage to the cellular components such as giving rise to the free radicals and reactive oxygen species (ROS).

Radiation can cause damage to a mammalian organism ranging from mild mutagenic and carcinogenic effects of low doses to almost instant killing by high doses. Overall radiosensitivity of the organism is determined by pathological alterations developed in several sensitive tissues that include hematopoietic system, reproductive system, and different epithelia with in certain cases a high rate of cell turnover.

The acute pathological outcome of gamma irradiation leading to death is different for different doses and is determined by the failure of certain organs that define the threshold of the organism's sensitivity to each particular dose. Thus, lethality at lower doses can occur from bone marrow aplasia, while moderate doses can kill faster by inducing gastrointestinal (GI) syndrome. At very high doses of radiation, instant death eliciting neuronal degeneration can occur.

A subject that is able to survive a period of acute toxicity of radiation can suffer from long term remote consequences that include radiation-induced carcinogenesis and fibrosis developing in exposed organs (e.g., kidney, liver or lungs) months and years after irradiation.

In certain embodiments, tumors are generally known to be more sensitive to gamma radiation and can be treated with multiple local doses that cause relatively low damage to normal tissue thus compositions disclosed herein can be used to prevent or treat the low level of damage. In accordance with these embodiments, use of gamma-irradiation during cancer therapy by conventional, three-dimensional conformal or more focused BeamCath delivery or other mode has dose-limiting toxicities caused by cumulative effect of irradiation and inducing the damage of the stem cells of rapidly renewing normal tissues, for example, bone marrow and gastrointestinal (GI) tract.

At high doses, radiation-induced lethality is associated with hematopoietic and gastrointestinal radiation syndromes. Hematopoietic syndrome is characterized by loss of hematopoietic cells and their progenitors, making it impossible to regenerate blood and lymphoid system. Death usually occurs as a consequence of infection (result of immunosuppression), hemorrhage and/or anemia. GI syndrome is caused by massive cell death in the intestinal epithelium, predominantly in the small intestine, followed by disintegration of intestinal wall and death from bacteriemia and sepsis. Hematopoietic syndrome usually prevails at the lower doses of radiation and leads to a more delayed death than GI syndrome.

In certain embodiments, a measure of protection for a particular composition or agent disclosed herein can be expressed by dose modification factor (DMF or DRF). DMF can be determined by irradiating a subject treated with a composition disclosed herein and irradiating untreated control subjects with ranges of radiation doses and then comparing the survival or some other endpoints. DMF is commonly calculated for 30-day survival (LD50/30 drug-treated divided by LD50/30 vehicle-treated) and quantifies the protection of the hematopoietic system. In order to estimate gastrointestinal system protection, LD50 and DMF are calculated for 6- or 7-day survival. DMF values provided herein are 30-day unless indicated otherwise. These experiments can be performed in an animal model such as a pig or other animal in order to support data presented herein.

There are needs for therapeutic agents to mitigate the side effects associated with chemotherapy and radiation therapy in the treatment of cancer. The use of AAT (isolated naturally occurring AAT, fragments thereof, analogs thereof, fusion molecules thereof or recombinant or synthetic AAT molecules or fragments) fulfills this need and provides other related advantages.

Accordingly, in one aspect, the invention provides compositions comprising AAT for use in minimizing, reducing and/or preventing radiation-induced cellular damage following intentional or accidental radiation exposure.

In some embodiments, the present invention relates to the use of α1-antitrypsin (AAT) and α1-antitrypsin-related polypeptides (e.g. fragments, peptides) to reduce the side effects of cancer treatments, such as radiation, in a subject. In accordance with this aspect of the invention, methods may be used to reduce, prevent, or treat one or more radiation induced side effects. Certain side effects include, but are not limited to myelosuppression, cellular toxicity, renal toxicity, weight loss, behavioral changes, pain, nausea, vomiting, diarrhea, constipation, anemia, malnutrition, hair loss, mouth sores, memory loss, hemorrhage, cardiotoxicity, hepatotoxicity, ototoxicity, and post-chemotherapy cognitive impairment. The behavioral change may be limited mobility. The composition may be administered prior to, concomitantly with, or after the radiation based cancer treatment.

In some embodiments, the methods include use of a composition including AAT to reduce or prevent side effects induced by a cancer treatment that includes radiation therapy in combination with chemotherapy. In accordance with these embodiments, chemotherapy can include, but is not limited to, cisplatinum, cyclophosphamide, doxorubicin, 5 fluorouracil, camptothecin, methotrexate, melphalan, taxanes, isosfamide, melphalan, hexamethyl-melamine, thiotepa, dacarbazine, cytarabine, 2-fluorodeoxycytidine, idatrexate, trimetrexate, vinblastine, vincristine, navelbine, estramustine, taxoids, etoposide, teniposide, daunorubicine, bleomycin, mitomycin, L asparaginase, topotecan, procarbazine, mitoxantrone, carboplatinum, interferon, and interleukin.

A composition comprising α1-antitrypsin (AAT) or other disclosed AAT-related composition may by used to protect normal cells in a mammal from conditions such as, but not limited to (1) cellular stress, which results from cancer treatments and hyperthermia; (2) exposure to harmful doses of radiation; for example, workers in nuclear power plants, or subjects living in proximity to nuclear power plants, the defense industry radiopharmaceutical production, or the military; and (3) cell aging. AAT may be used to protect such radiation- and chemotherapy-sensitive tissues as the hematopoietic system (including immune system), the epithelium of the gut, and hair follicles.

In certain embodiments, methods and compositions disclosed herein provide for modes of reducing or preventing cellular damage induced by radiation exposure in a subject in need thereof, comprising administering to the subject a composition comprising alpha-1 antitrypsin (AAT) or fragment thereof.

In some embodiments, the methods of the invention can be used to treat mammalian subjects, such as human subjects exposed to from about 200 cGY up to 1000 cGY, such as from 200 cGY up to 800 cGY, in order to reduce or prevent radiation induced cellular damage or other radiation side effects.

In some embodiments, the composition for use in the invention comprises human α1-antitrypsin (hAAT). hAAT is a glycoprotein of MW 51,000 with 417 amino acids and 3 oligosaccharide side chains. hAAT is a single polypeptide chain with no internal disulfide bonds and only a single cysteine residue normally intermolecularly disulfide-linked to either cysteine or glutathione. The reactive site of AAT contains a methionine residue, which is labile to oxidation upon exposure to tobacco smoke or other oxidizing pollutants. Such oxidation reduces the elastase-inhibiting activity of AAT; therefore, substitution of another amino acid at that position, i.e., alanine, valine, glycine, phenylalanine, arginine or lysine, produces a form of AAT which is more stable.

Some embodiments disclosed herein concern treating a subject having or suspected of developing prostate cancer. In accordance with these embodiments, a male subject having or suspected of developing prostate cancer can be treated with compositions disclosed herein before, during or after radiation therapy treatment(s) in order to reduce side effects attributed to these therapies. For example, side effects can be, but are not limited to, development of impotence or erectile dysfunction.

In certain embodiments, the subject is a mammal. In some embodiments, the mammal is a human. In other embodiments, the mammal is a non-human mammal. In yet other embodiments, the subject is a male, a female, a pregnant female or young child or infant.

A large number of accidents have occurred over the years involving radiation materials and sources. People and animals have died from causes attributed to excessive radiation exposure and others have suffered permanent debilitating injuries. In some of these situations, the excessive radiation exposure was due to accidents or safety breaches that result large amounts of radiation being leaked or spread to outlying areas. In certain embodiments, it is contemplated that a subject exposed to such radiation can be treated by compositions disclosed herein in order to reduce or eliminate adverse effects of radiation therapy, for example, as a radioprotectant agent for non-cancerous cells or tissue. The severity of radiation's effects can depend on many other factors such as the magnitude and duration of the dose; the area of the body exposed to it; and a subject's sex, age, and physical condition.

Embodiments herein provide for methods and compositions for treating a subject having cancer or other medical condition treated by radiation therapy. In accordance with these embodiments, the composition may include, but is not limited to, alpha-1 antitrypsin, a carboxyterminal peptide derived therefrom (e.g. a carboxyternminal peptide of AAT found in the last 80 amino acids of AAT), an analog thereof, or fusion molecule thereof. In some embodiments, exogenous human derived AAT (e.g. wholly or partially purified from human blood) can be used in treatments contemplated herein. In other embodiments, commercially available AAT compositions can be used to treat a subject described herein.

In some embodiments, compositions can be administered to a subject based on time course and extent of cancer therapy regimen. In some embodiments, compositions disclosed herein can be administered to a subject before, during or after cancer therapy regimen. In other embodiments, compositions disclosed herein can be administered to a subject within 48 hours of an event (e.g. immediately or about 24 hours after the treatment). In certain embodiments, compositions disclosed herein can be administered to a subject several days to weeks after radiation therapy, for example 5 days, 7 days, 2 weeks or more. It is contemplated that a subject having or suspected of developing cancer can be treated continuously or at pre-determined intervals to reduce adverse effects to the radiation.

In other embodiments, a composition may further include, but is not limited to, an anti-inflammatory agent, an immunosuppressive agent, an immunomodulatory agent, an anti-microbial agent, an anti-viral agent, an anti-bacterial agent, other known anti-cancer treatments and a combination thereof.

AAT

Human AAT is a single polypeptide chain with no internal disulfide bonds and only a single cysteine residue normally intermolecularly disulfide-linked to either cysteine or glutathione. One reactive site of AAT contains a methionine residue, which is labile to oxidation upon exposure to tobacco smoke or other oxidizing pollutants. Such oxidation reduces the elastase-inhibiting activity of AAT; therefore substitution of another amino acid at that position, e.g., alanine, valine, glycine, phenylalanine, arginine or lysine, produces a form of AAT which is more stable. Native AAT can be represented by the following or other formulas (e.g. SEQ ID NO:39):

(SEQ ID NO: 1)
EDPQGDAAQKTDTSHHDQDHPTFNKITPNLAEFAFSLYRQLAHQSNSTNIFFSPVS

IATAFAMLSLGTKADTHDEILEGLNFNLTEIPEAQIHEGFQELLRTLNQPDSQLQLTTGN

GLFLSEGLKLVDKFLEDVKKLYHSEAFTVNFGDTEEAKKQINDYVEKGTQ

GKIVDLVKELDRDTVFALVNYIFFKGKWERPFEVKDTEEEDFHVDQVTTVKVPMMKRLG

M FNIQHCKKLSSWVLLMKYLGNATAIFFLPDEGKLQHLENELTHDIITKFLENEDRRSASL

HLPKLSITGTYDLKSVLGQLGITKVFSNGADLSGVTEEAPLKLSKAVHKAVLTIDEKGTE

AAGAMFLEAIPMSIPPEVKFNKPFVFLMIEQNTKSPLFMGKVVNPTQK.

AAT polypeptide of use herein can be isolated and/or purified from a mammalian subject, or chemically synthesized by standard methods, or can be produced recombinantly or a fragment thereof. The synthesis of the presently disclosed compounds can be accomplished using standard chemical reactions known to be useful for preparing a variety of analogous compounds. Indeed, exemplary techniques known to those of ordinary skill in the art of peptide synthesis are taught by Bodanszky & Bodanszky (The Practice of Peptide Synthesis; Springer Verlag, New York, 1994) and by Jones (Amino Acid and Peptide Synthesis; 2nd ed.; Oxford University Press, 2002), both of which are incorporated herein by reference. The Bodanszky and Jones references detail the parameters and techniques for activating and coupling amino acids and amino acid derivatives. Moreover, the references teach how to select, use and remove various useful protecting groups. An exemplary specific process for (poly)peptide production is described in Lu et al. (Fed. Europ Biochem Societies Lett 429:31-35, 1998).

AAT polypeptides for use in the methods of the invention can also be made according to recombinant DNA methods, by expressing a recombinant polynucleotide sequence that encodes for the AAT polypeptide (SEQ ID NO:1) in a suitable host cell. Generally, the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eukaryotic or prokaryotic host cell, and culturing the host cell thus transformed. When a eukaryotic host cell is used, the compound may optionally include a glycoprotein portion. Viral vectors can also be prepared encoding the polypeptides disclosed herein. Many viral vectors have been constructed and are known to those of skill in the art.

Variant therapeutic polypeptides include polypeptides that differ in amino acid sequence from the disclosed sequence set forth as SEQ ID NO:1, but that share structurally significant sequence homology with SEQ ID NO:1, such as at least 80%, at least 85%, at least 90%, at least 95%, or at least 96%, or at least 97%, or at least 98%, or at least 99% homology and retain therapeutic properties of AAT described herein. Such variants may be produced by manipulating the nucleotide sequence of the encoding sequence, using standard procedures, including site-directed mutagenesis or PCR. Certain modifications concern substitution of one or more amino acids for amino acids having similar biochemical properties, conservative substitutions. One of ordinary skill in the art will be able to predict or empirically determine (particularly in view of the provided teachings) amino acids that may be substituted for an original amino acid in a peptide.

In certain embodiments, compositions of AAT or AAT-derived carboxyterminal peptides capable of binding to SEC receptors or compositions with AAT-like activities may be administered to a subject in need thereof. As disclosed herein the carboxy terminal region of AAT includes the last 80 amino acids of SEQ ID NO:1 or human AAT molecule or other naturally occurring AAT molecule. In other embodiments, peptides derived from AAT can include 5-mers, 10-mers, 20-mers, 25-mers, 30-mers, 35-mers, 40-mers, 50-mers, and up to an 80 mer of an AAT molecule wherein any of the contemplated peptides have no significant serine protease inhibitor activity, are derived from the carboxyterminus of AAT and are capable of being used for treating subjects undergoing radiation or subjects exposed to large doses of radiation by accident or other cause.

In one embodiment of the present invention, a composition may include compounds that engage molecules for the SEC receptor to treat a subject. In some of the recited methods, an AAT-mutant or AAT derived peptide (e.g. mammalian derived) having no significant serine protease inhibitor activity contemplated for use within the methods of the present invention can include a series of peptides including carboxyterminal amino acid peptides corresponding to AAT. Among this series of peptides, some include, but are not limited to pentamers or pentameric derivatives of an AAT region, including, but not limited to, FVFLM (SEQ ID NO:2), FVFAM (SEQ ID NO:3), FVALM (SEQ ID NO:4), FVFLA (SEQ ID NO:5), FLVFI (SEQ ID NO:6), FLMII (SEQ ID NO:7), FLFVL (SEQ ID NO:8), FLFVV (SEQ ID NO:9), FLFLI (SEQ ID NO:10), FLFFI (SEQ ID NO:11), FLMFI (SEQ ID NO:12), FMLLI (SEQ ID NO:13), FIIMI (SEQ ID NO:14), FLFCI (SEQ ID NO:15), FLFAV (SEQ ID NO:16), FVYLI (SEQ ID NO:17), FAFLM (SEQ ID NO:18), AVFLM (SEQ ID NO:19), and any combination thereof.

In addition, combinations of amino acid 5-mers or 10-mers or 20-mers or 30-mers or more can also be used. For example, one or more 5-mers or 10-mers or 20-mers etc can include consecutive amino acids starting from AA 315 and ending with AA 394 of naturally occurring AAT represented as SEQ ID NO:38. Other examples contemplated herein can include compositions of SEQ ID NO:2 through SEQ ID NO:39 which may be combined or made into a mixture or made into concatamers and administered to a subject.

As contemplated herein, the later half of a sequence toward the carboxy end is referred to as the carboxyterminus. In certain embodiments, the carboxyl domain of AAT going backwards from the carboxyl terminus is defined as those amino acids most conserved among the difference species and do not participate in the protease binding domain of AAT. In addition, in other embodiments, AAT protease binding domain can be mutated in order to reduce or eliminate the protease function of the molecule and this molecule can be used in any composition contemplated herein. In other embodiments, a mutated molecule can retain its anti-inflammatory effects. Also contemplated herein is that the carboxyl domain is the non-protease binding domain. One skilled in the art would understand a non-protease binding domain of AAT.

In each of the above-recited methods, compositions herein may include peptides derived from the carboxyterminus of AAT. The peptides may include but are not limited to amino acid peptides selected from one or more of LSGVTEEAPL (SEQ ID NO:20); KLSKAVHKAV (SEQ ID NO:21); LTIDEKGTEA (SEQ ID NO:22); AGAMFLEAIP (SEQ ID NO:23); VSIPPEVKFN (SEQ ID NO:32); MSIPPEVKFN (SEQ ID NO:24); KPFVFLMIEQ (SEQ ID NO:25); NTKSPLFMGK (SEQ ID NO:26); VVNPTQK (SEQ ID NO:27), GADLSGVTEE (SEQ ID NO:28); APLKLSKAVH (SEQ ID NO:29); KAVLTIDEKG (SEQ ID NO:30); TEAAGAMFLE (SEQ ID NO:31); RIPVSIPPEV (SEQ ID NO:32); KFNKPFVFLM (SEQ ID NO:33); IEQNTKSPLF (SEQ ID NO:34); MGKVVNPTQK (SEQ ID NO:35); LEAIPMSIPPEVKFNKPFVFLM (SEQ ID NO:36); and LEAIPMSIPPEVKFNKPFVF (SEQ ID NO:37), GADLSGVTEE-APLKLSKAVHKAV LTIDEKGTEAAGAMFLERIPV SIPPEVKFNKPFVFLMIEQNTKSPLFMGKVVNPTQK (SEQ ID NO:38) or any combination thereof. It is contemplated that the AAT-derived peptides from the carboxyterminus recited for use in the compositions and methods herein are also intended to include any and all of those specific AAT peptides other than the 10 amino acid AAT peptides of SEQ ID NO:1 depicted supra. For example, while AAT peptides amino acids 315-324, amino acids 325-334, amino acids 335-344, etc of SEQ ID NO:1 have been enumerated herein, it is intended that the scope of the compositions and methods of use of same specifically include all of the possible combinations of AAT peptides such as amino acids 316-325, amino acid 317-326, 318-327, etc. of SEQ ID NO:1, as well as any and all AAT peptide fragments corresponding to select amino acids of SEQ ID NO:1, without actually reciting each specific AAT peptide of SEQ ID NO:1 therewith. Thus, by way of illustration, and not by way of limitation, Applicants are herein entitled to possession of compositions based upon any and all AAT peptide variants based upon the amino acid sequence depicted in SEQ ID NO:1 and use of such compositions in the methods of the present invention.

In certain embodiments, AAT-associated molecules used in the methods and compositions herein can include, but are not limited to, compositions of SEQ ID NO:1, naturally occurring AAT (394 AA length molecule making up approximately 90% of AAT isolated from serum), or other AAT compositions such as, Aralast™ (Baxter), Zemaira™ (Aventis Behring), Prolastin™, Prolastin C™ (Grifols, N.C.), Aprotonin™ or Trasylol™ (Bayer Pharmaceutical Corporation), Ulinistatin™ (Ono Pharmaceuticals, Inc.), and inhalation and/or injectable AAT (Kamada, Ltd., Israel, aerosol or other formulations), or any other commercially available AAT compositions or any combination thereof.

In accordance with embodiments of the present invention, the peptide can be protected or derivatized in by any means known in the art for example, N-terminal acylation, C-terminal amidation, cyclization, etc. In a specific embodiment, the N-terminus of the peptide is acetylated.

Other embodiments concern mutants of human AAT (hAAT) where the mutant is generated to have no significant serine protease inhibitor activity. Any method known in the art for generating mutants is contemplated. Some embodiments include using site-directed mutagenesis to generate a hATT having no significant serine protease inhibitor activity (e.g. hAAT with a single amino acid (AA) change in the reactive center loop (RCL) at proline, for example replacing the proline with a cysteine; or heat inactivated formulations). Other methods include disrupting the serine protease inhibiting region or keeping the RCL intact while changing one or more AAs of hAAT using a disruption method or using heated hAAT to reduce or eliminate serine protease inhibition activity, or generating a mutant (e.g. RCL mutant with a modified cysteine), or chemically modifying hAAT to eliminate or dramatically reduce serine protease inhibitor activity.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regimen may be adjusted to provide the optimum therapeutic response. Pharmaceutical compositions that include AAT polypeptides or a functional variant thereof (or nucleic acid molecules encoding AAT polypeptides) as an active ingredient may be formulated with an appropriate solid or liquid carrier, depending upon the particular mode of administration chosen. Pharmaceutical compositions may include additional cytoprotective or radioprotective agents known to the art (for example, as described in Tofilon, Chem. Rev. 109:2974-88, 2009).

Dosage form of the pharmaceutical composition can be determined by the mode of administration chosen. For instance, in addition to injectable fluids, inhalational, topical, ophthalmic, peritoneal, and oral formulations can be employed. Inhalational preparations can include aerosols, particulates, nasal sprays, inhalers and similar preparations.

In general, the goal for particle size for inhalation is about 1 µm or less in order that the pharmaceutical reach the alveolar region of the lung for absorption. Oral formulations may be liquid (for example, syrups, solutions, or suspensions) or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

Pharmaceutical compositions disclosed herein can be administered by any route known in the art, including, but not limited to, parenteral administration; for example, intravenous, intramuscular, intraperitoneal, intrasternal, or intra-articular injection or infusion, or by sublingual, oral, topical, intra-nasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

In certain embodiments, active compounds (e.g., peptides, proteins, oligos) can be suitably administered by sustained-release systems or slow release formulations. Suitable examples of sustained-release formulations include suitable polymeric materials (such as, for example, semi-permeable polymer matrices in the form of shaped articles, for example, films or microcapsules), suitable hydrophobic materials (for example, as an emulsion in an acceptable oil), suitable microparticles or microbeads, or ion exchange resins, and sparingly soluble derivatives (such as, for example, a sparingly soluble salt). Sustained-release compounds may be administered by intravascular, intravenous, intra arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray. Pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance.

A suitable administration format may best be determined by a medical practitioner for each subject individually. Various pharmaceutically acceptable carriers and their formulation are described in standard formulation treatises, for example, Remington's Pharmaceutical Sciences by E. W. Martin. See also Wang and Hanson, J. Parenteral Sci. Technol., Technical Report No. 10, Supp. 42: 2S, 1988.

In some embodiments, therapeutic agent(s) can be delivered by way of a pump (see Sefton, CRC Crit. Ref. Biomed. Eng. 14:201, 1987; Buchwald et al., Surgery 88:507, 1980; Saudek et al., N. Engl. J. Med. 321:574, 1989) or by continuous subcutaneous infusions, for example, using a mini-pump. An intravenous bag solution may also be employed. In another aspect of the disclosure, therapeutic agent(s) are delivered by way of an implanted pump. Implantable drug infusion devices are used to provide subjects with a constant and long term dosage or infusion of a drug or any other therapeutic agent. Essentially, such device may be categorized as either active or passive.

Pharmaceutical compositions containing AAT or peptide fragment thereof, or analog thereof, or mutant thereof, or a functional derivative thereof (e.g. pharmaceutical chemical, protein, peptide of some of the embodiments) may be administered to a subject, for example by subcutaneous, intravenous, intracardiac, intracoronary, intramuscular, by oral administration, by inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the composition may be administered intranasally, such as inhalation.

Some embodiments disclosed herein concern using a stent or a catheter to deliver one or more chemotherapeutic agents (e.g. along with compositions disclosed herein) to a subject having or suspected being treated for cancer. Any stent or other delivery method known in the art that can deliver one or more agents directly to tumor site is contemplated. These delivery techniques can be used alone or in combination with other delivery methods.

A compound (e.g. a peptide, protein or mixture thereof) may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used.

Sterile injectable solutions can be prepared by incorporating active compound in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art. Solutions of the active compounds as free-base or pharmacologically acceptable salts can be prepared in water suitably mixed with a surfactant, such as hydroxypropylcellulose.

A composition including AAT may be administered prior to, during, or after exposure to radiation, or a combination thereof. In some embodiments, one or more doses of the composition of AAT can be administered to a subject, such as a human subject, within a week prior to radiation exposure, such as within 5 days, 4 days, 3 days, 48 hours, or from 1-24 hours prior to radiation exposure. In some embodiments, the composition including AAT can be administered to a subject during exposure to radiation. In some embodiments, one or more doses of the composition including AAT can be administered to a subject within 1 hour to 30 days (or longer) after exposure to radiation, such as within 14 days, within 7 days, within 5 days, within 4 days, within 3 days, within 48 hours, or within 1-24 hours after exposure to radiation. In some embodiments, administration can include at least one dose of AAT from about 1 to 100 mg/kg within 48 hours prior to exposure to within 48 hours after radiation exposure. In some embodiments, the administration further includes at least two or more doses of AAT from about 1 to 100 mg/kg every 24 to 48 hours for a period of from 2 days to 30 days after radiation exposure. In some embodiments, the administration includes at least one dose of AAT from about 1 to 100 mg/kg prior to radiation exposure. In some embodiments, the administration comprises at least one dose of AAT within 24 hours prior to the time of radiation exposure. In some embodiments, a subject can be treated with about 40 to about 80 mg/kg of AAT or derivative or fragment thereof.

In some embodiments, the administration comprises a dose of AAT from about 1 to 100 mg/kg at least once prior to radiation exposure, such as within 24 hours prior to radiation exposure, and periodic doses of AAT (1 to 100 mg/kg) every 24-48 hours thereafter, up to a total of at least 10 or more doses over a period of from at least 10 to 20 days after radiation exposure. In some embodiments, administration of the composition comprising AAT is intravenous or intra-peritoneal.

In another embodiment, nasal solutions or sprays, aerosols or inhalants may be used to deliver the compound of interest (e.g AAT). Additional formulations that are suitable for other modes of administration may include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Liposomes or microparticles can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In some embodiments, compositions and methods concern a compound having no significant serine protease inhibitor activity but having other α1-antitrypsin activity or analog thereof may be used in a single therapeutic dose, acute manner or a chronic manner to treat a subject.

Radiation Applications

Radiation therapy can be administered in a variety forms including external beam radiation using different sources of radiation such as gamma rays produced by cobalt 60 or proton irradiation using a particle accelerator. It can also be done using radioactive beads, seed, microparticle or microspheres that are placed into the tumor or tissue to be irradiated. External beam irradiation is generally done in fractionated doses with the beam focused as narrowly as possible on the tumor or tissue to be therapeutically irradiated. The use of a fractionated dose helps minimize the side effects of the radiation on normal tissues and achieve a higher total dose to maximize tumor control or eradication. The number of fractions can vary, and may, for example be given three times per week for 8 weeks for a total 24 fractions. Many other regimens for treatment exist based for example, on the type of cancer being treated, the stage of the cancer and the subject involved.

Isolated Proteins

One embodiment pertains to isolated proteins, and biologically active peptides thereof. In one embodiment, the native polypeptide can be isolated from cells or tissue sources by an appropriate purification scheme using standard protein purification techniques. In certain embodiments, the native polypeptide may be heated or otherwise treated to reduce or eliminate serine protease inhibitor activity. In certain particular embodiments, serine protease inhibitor activity is reduced where no significant activity remains. In another embodiment, polypeptides contemplated herein are produced by recombinant DNA techniques. Alternative to recombinant expression, a polypeptide can be synthesized chemically using standard peptide synthesis techniques. Any of the peptide or protein molecules contemplated of use in compositions disclosed herein can be compositions having no significant serine protease inhibitor activity. For example, AAT compositions may be treated in order to reduce or eliminate serine protease inhibitor activity or an AAT polypeptide may be isolated wherein the polypeptide has reduced or no significant serine protease inhibitor activity.

An "isolated" or "purified" protein or biologically active portion thereof is substantially free of cellular material or other contaminating proteins from the cell or tissue source from which the protein is derived, or substantially free of chemical precursors or other chemicals when chemically synthesized. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

In certain embodiments, polypeptides can include a polypeptide having a consecutive amino acid sequence corresponding to a portion or all of the last 80 amino acids of carboxyterminus of AAT or AAT allele. Other useful proteins are substantially identical to any portion of the carboxyterminus, and retain the functional activity of the peptide of the corresponding naturally-occurring protein other than serine protease inhibitor activity yet differ in amino acid sequence due to natural allelic variation or mutagenesis.

Some compositions disclosed herein may be used as therapeutic agents in the treatment of a physiological condition caused in whole or part, by excessive serine protease activity. In addition, a physiological condition can be inhibited in whole or part. Peptides contemplated herein may be administered in a composition as free peptides or pharmaceutically acceptable salts thereof. Peptides may be administered to a subject as a pharmaceutical composition, which, in most cases, will include the peptide and/or pharmaceutical salts thereof with a pharmaceutically acceptable carrier.

Biologically active portions of a polypeptide of the invention include polypeptides including amino acid sequences sufficiently identical to or derived from the amino acid sequence of the protein (e.g., the amino acid sequence shown in any of SEQ ID NOs:2 to 38, which exhibit at least one activity of the corresponding full-length protein). A biologically active portion of a protein of the invention can be a polypeptide, which is, for example, 5, 10, 20, 30, 40 or more amino acids in length. Moreover, other biologically active portions having no significant serine protease inhibitor activity, in which other regions of the protein are deleted, can be prepared by recombinant techniques and evaluated for one or more of the functional activities of the native form of a polypeptide disclosed herein.

In certain embodiments, polypeptides may have the amino acid sequence of SEQ ID NOs:1 to 38. Other useful proteins are substantially identical (e.g., at least about 45%, preferably 55%, 65%, 75%, 85%, 95%, or 99%) to any of SEQ ID NOs:1 to 39.

Variants of AAT molecules having no significant serine protease activity can be generated by mutagenesis, e.g., discrete point mutation or truncation. For example, a point mutation may be generated in AAT or peptide derivative thereof that still leaves the reactive center loop intact (RCL) while interfering with or preventing serine protease binding capabilities with the AAT or peptide but retaining its ability to modulate radiation adverse effects. An agonist can retain substantially the same, or a subset, of the biological activities of the naturally occurring form of the protein except no significant serine protease activity remains. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Fusion Polypeptides

In other embodiments, agents such as AAT and/or analog thereof, or peptide derivative thereof may be part of a fusion polypeptide. In one example, a fusion polypeptide may include AAT (e.g. naturally occurring mammalian α1-antitrypsin) or an analog thereof and a different amino acid sequence that may be heterologous to AAT or analog substance. In addition, a fusion polypeptide disclosed herein can include a pharmaceutically acceptable carrier, excipient or diluent. Any known methods for generating a fusion protein or fusion peptide are contemplated herein.

In yet another embodiment, AAT polypeptide or peptide fusion protein can be a GST fusion protein in which is fused to the C-terminus of GST sequences. Fusion expression vectors and purification and detection means are known in the art. Expression vectors can routinely be designed for expression of a fusion polypeptide of the invention in prokaryotic (e.g., E. coli) or eukaryotic cells (e.g., insect cells (using baculovirus expression vectors), yeast cells or mammalian cells) by means known in the art. In yet another embodiment, a nucleic acid of the invention is expressed in mammalian cells using a mammalian expression vector as described in the art.

Combination Therapies

Any of the embodiments detailed herein may further include one or more a therapeutically effective amount of cancer-related medications. These therapies can include, but are not limited to, aspirin and other antiplatelet therapy including for example, clopidogrel, prasugrel, ticagrelor, abciximab, eptifibatide, tirofiban; heparin and derivatives; direct thrombin inhibitors or Xa inhibitors; warfarin; angiotensin converting enzyme inhibitors or angiotensin receptor blockers; beta- and alpha-adrenergic receptor blockers; calcium channel blockers; HMGCoA reductase inhibitors (e.g. statins); niacin and derivatives; fenofibrate; fish oil; aldosterone blockers; hydralazine and nitroderivates; phosphodiesterase inhibitors; direct guanylil cyclase activators, antimicrobial drugs, anti-inflammatory agent, immunomodulatory agent, or immunosuppressive agent or combination thereof.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxuline.

Anti-parasitic agents contemplated of use herein can include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole, (sulfamethoxazole/trimethoprim), and pentamidine isethionate.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents which treat the immune, vascular, or lymphatic systems or any combination thereof.

Anti-inflammatory or immunomodulatory drugs or agents contemplated of use herein can include, but are not limited to, interferon derivatives, e.g., betaseron, β-interferon; prostane derivatives, iloprost, cicaprost; glucocorticoids such as cortisol, prednisolone, methylprednisolone, dexamethasone; immunsuppressive agents such as cyclosporine A, FK-506, methoxsalen, thalidomide, sulfasalazine, azathioprine, methotrexate; lipoxygenase inhibitors, e.g., zileutone, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukines, other cytokines, T-cell-proteins; antibodies against receptors of interleukins, other cytokines, and T-cell-proteins.

Other agents of use in combination with compositions herein can be molecules having serine protease inhibitor activity. For example other serine protease inhibitors contemplated of use herein can include, but are not limited to, leukocyte elastase, thrombin, cathepsin G, chymotrypsin, plasminogen activators, and plasmin.

In addition, other combination compositions of methods disclosed herein can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. In certain embodiments, antibody-based therapies may be used as induction therapy in combination with the compositions and methods disclosed herein.

Subjects contemplated herein can include human subjects, male or female, adult or infant, or fetus, or other subjects such as non-human subjects, including but not limited to, primates, dogs, cats, horses, cows, pigs, guinea pigs, birds and rodents.

Kits

In still further embodiments, kits for use with the methods described above are contemplated. Kits may include AAT, one or more peptides derived from AAT, a mutant AAT composition, a mutant AAT molecule associated with a gene therapy delivery system or other combinations. Small molecules, proteins or peptides may be employed for use in any of the disclosed methods. In addition, other agents such as antibacterial agents, immunosuppressive agents, anti-inflammatory agents may be provided in the kit. The kits can include, suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means or other delivery device (e.g. a stent or catheter). A kit will also generally contain a second, third or other additional container into which other combination agents may be placed. Such containers may include injection or blow-molded plastic containers into which the desired vials are retained.

In certain embodiments, a kit can include a composition including, but not limited to, AAT, AAT fragment, or an AAT analog or polypeptide, having no significant serine protease inhibitor activity. In accordance with these embodiments, a kit can contain AAT or an analog thereof having no significant serine protease inhibitor activity. Further embodiments may include an AAT composition alone or in combination with a chemotherapy agent. It is contemplated herein the AAT can be administered as a separate composition from a chemotherapeutic agent or as a combined composition taking into account the specific environment required for each active agent. These formulations may include a slow release formulation such as a microparticle or other delivery composition. Other kits may include a portable means of administering radiation in combination with AAT compositions.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the some embodiments which are disclosed and still obtain a like or similar result without departing from the spirit and scope of the invention.

Example 1

This exemplary experiment illustrates that administration of α1-antitrypsin ("AAT") to an acceptable mouse model protects the mice from radiation induced tissue necrosis and increases survival after radiation exposure.

Methods and Materials:

Measuring the Effect of AAT Administration on Radiation Induced Tissue Necrosis in Mice C57/BL6J mice (H-$2^b$) (Jackson Laboratory, Bar Harbor, Me.), 10-14 weeks old with average body weight of 28 g, received single-dose total body irradiation (TBI) with 800-1000 cGy. Mice in the experimental group were given AAT intra-peritoneally at 3 mg/dose, (purified hAAT (Aralast; Baxter, Deerfield, Ill.) suspended in 125 µl, 24 hours (Day −1 or "D−1") before irradiation and every 2 days post-irradiation for a total of 10 injections. Mice in the control group were injected, also intra-peritoneally, with 125 µl of human albumin on the same schedule. Each group in the initial experiment measuring the effect of AAT on 800, 1000 and 1200 consisted of 3 mice.

Body weights were obtained and recorded on day 0 and weekly thereafter. A weekly clinical index was generated by summation of 5 criteria scores: percentage of weight change, posture (hunching), activity, fur texture, and skin integrity (maximum score=10). Animals that received a score of 6.5 or higher were killed using $CO_2$ euthanasia.

Blood samples were collected sequentially for cytokine assays. To determine the presence of various cytokines in the two groups of mice, we used the mouse proteome profiler array membrane kit Panel A (ARY006; R&D Systems, Minneapolis, Minn.) according to the manufacturer's instructions. Equal volumes (100 µl) of plasma were collected from individual animals and added to the precoated membranes of the kit. The dot blot membranes (standardized for loading control) were analyzed using ImageQuant software (Molecular Dynamics, Sunnyvale, Calif.).

Histopathology

At autopsy skin, stomach and small bowel samples were obtained from AAT and albumin-treated mice, fixed in 4% paraformaldehyde, and embedded in paraffin before sectioning. The sections were stained with hematoxylin-eosin to assess for inflammatory lesions by light microscopy. The frequencies and severity of inflammatory lesions were estimated and compared between groups. At least 3 sections from each organ were scored.

Cell Separation and Reagents

WBC were separated by Dextran sedimentation (early after HCT when blood cell counts were low) and PBMC were separated by Ficoll-Hypaque density gradient centrifugation (in patients with chronic GVHD). RNA was extracted from WBC and PBMC using Trizol as previously described (Deeg, H. J., et al., Blood 96 (Part 1):146a, #625, 2000). cDNA synthesis was performed from 500 ng of total RNA using Invitrogen Superscript RT (Invitrogen, Carlsbad, Calif.). Goat polyclonal anti-human IL-32 antibody AF3040 was obtained from R&D Systems (Minneapolis, Minn.), rabbit polyclonal anti-β actin antibody from Santa Cruz Biotechnology (Santa Cruz, Calif.), and each used according to the manufacturers' recommended conditions. Concanavalin A was purchased from Sigma-Aldrich Co (St. Louis, Mo.); Aralast NP (human α-1-antitrypsin), a serum serine-protease inhibitor that blocks the enzymatic activity of neutrophil elastase, cathespin G, PR3, thrombin, trypsin, and chymotrypsin, was purchased from Baxter (Westlake Village, Calif.).

Figure 1:
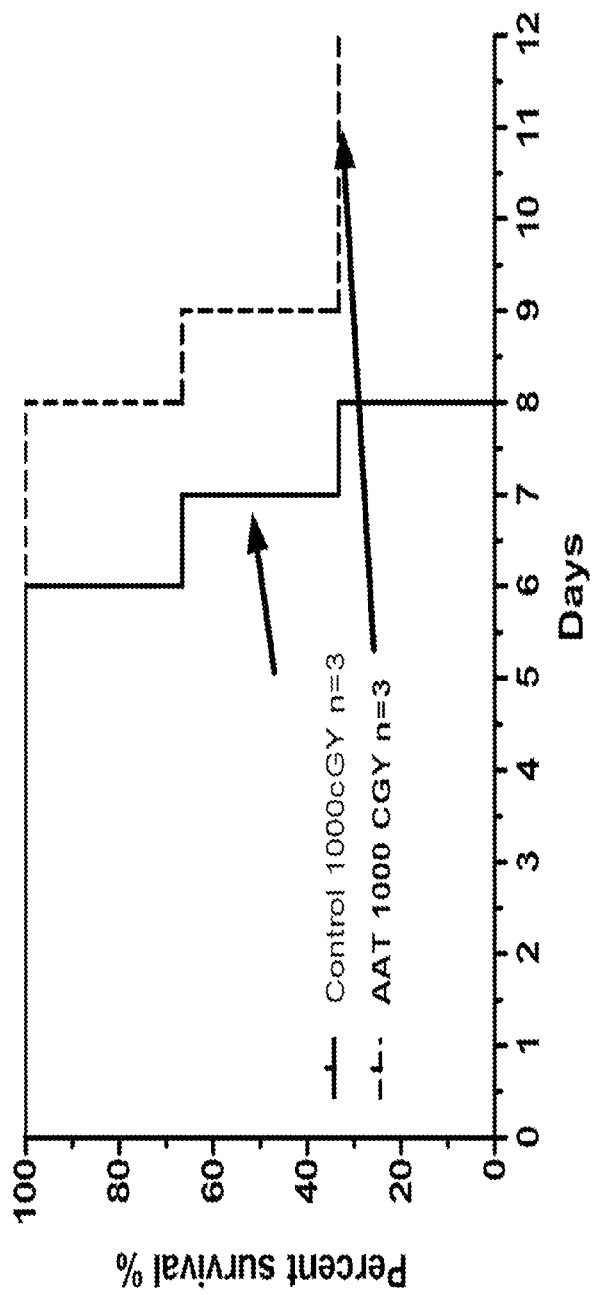
FIG. 1 represents an exemplary graphic illustration of radiation protection of mice having received AAT treatment pre and post TBI (total body irradiation) irradiation at a dose of 1000 cGY, as described in Example 1.

Results:

FIG. 1 graphically illustrates radiation protection of mice that received AAT treatment pre and post TBI irradiation at a dose of 1000 cGY. As shown in FIG. 1, treatment with AAT increased survival of the mice, such that by day 8, 60% of the mice were alive, and by day 12 (the last day measured), 30% of the mice were alive, whereas the control mice that received albumin (and did not receive AAT) died by day 8 after radiation exposure. Similar results were observed after 800 cGY.

Figure 2:
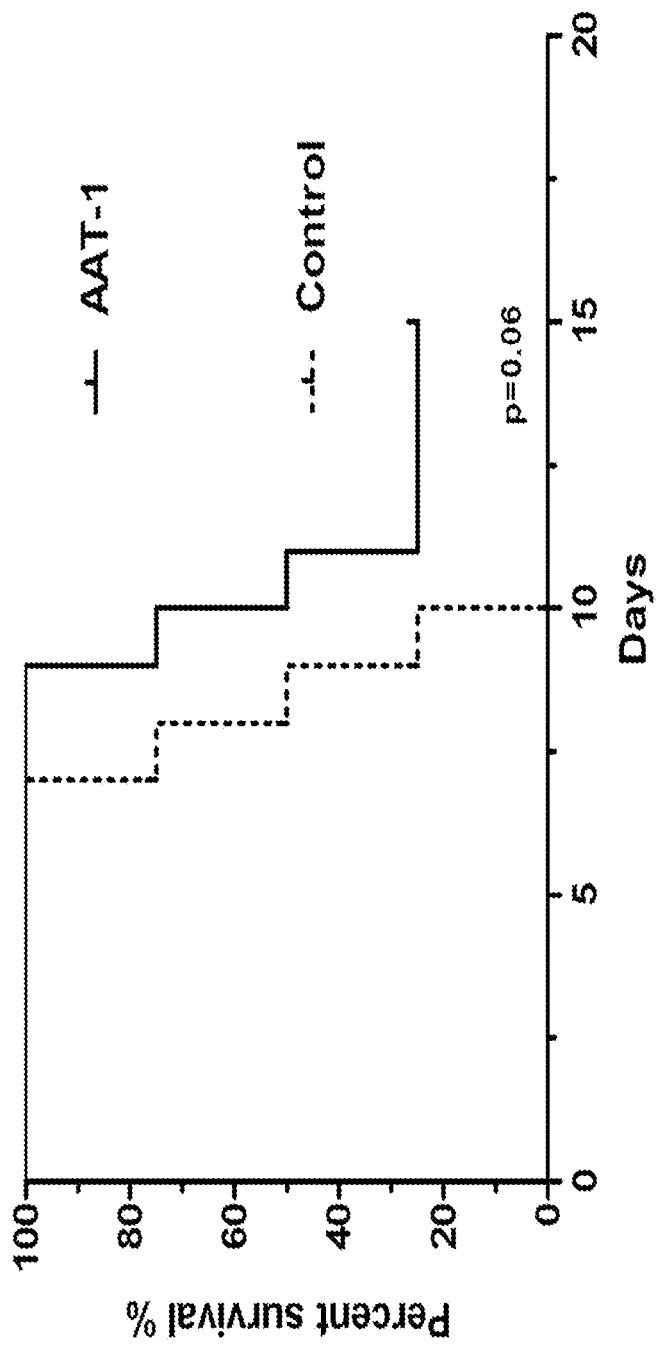
FIG. 2 represents an exemplary graphic illustration of percent survival of mice in an experiment in which mice (n=4) were treated with 3 mg/animal AAT at 24 hours (Day −1) before irradiation with 1000 cGy and a dose of 3 mg/animal AAT every 48 hours after irradiation for several days, as described in Example 1.

FIG. 2 graphically illustrates percent survival of mice in an experiment in which mice (n=4) were treated with 3 mg/animal AAT at 24 hours (Day −1) before irradiation with 1000 cGY and a dose of 3 mg/animal AAT every 48 hours after irradiation (q48 h) for 10 days. The Control mice (n=4) were treated with albumin and irradiated with 1000 cGY (with no AAT treatment). As illustrated in FIG. 2, treatment with AAT pre irradiation was instrumental in the prevention of radiation toxicity.

FIG. 3 graphically illustrates the percent survival of mice in an experiment in which mice (n=4) were treated with 3 mg/animal AAT only after the irradiation (24 hours post exposure) with subsequent doses of 3 mg/animal of AAT every 48 hours thereafter for 10 days. The Control mice (n=4) were treated with albumin and irradiated with 1000 cGY (with no AAT treatment). As shown in FIG. 3, the AAT administered after exposure to irradiation did not improve survival of the mice in comparison to the control mice.

FIG. 4 graphically illustrates the protein levels of various cytokines assayed in serum obtained from the mice treated with AAT 24 hours prior to and every 48 hours after exposure to 1000 cGy radiation, and the control mice, as determined on Day 10 after irradiation. The bars in the graph represent the optic interpretation of dot blot analysis. Changes in cytokine concentration are expressed as percent change compared to the albumin control treated animals. The horizontal dotted lines shown in FIG. 4 indicate an increase or decrease of 25% in cytokine concentration in the AAT treated mice as compared to the Albumin treated control mice. As shown in FIG. 4 the only up-regulated cytokine is IL 1RA. It is noted that TNF-α and other proinflammatory cytokines are reduced in the AAT treated mice.

This data illustrates that intervening with AAT compositions at an early tissue response to radiation is of therapeutical interest. Cytokines such as TNF-α and IL-1β can be downregulated, as mediated thru up-regulating IL-1RA expression. This experimental approach also demonstrates a decrease of the cytokine-mediated events in the normal tissues following AAT administration in comparison with the appropriate controls. This intervention resulted in increased survival of the mice in the accepted mouse model. Sustained inhibition of cytokines by AAT which was observed for several days after periodical Intra-Peritoneal injection in mice could potentially interrupt a link between early cytokine production, and thus exert a prolonged protection effect. In this study, it was demonstrated that radiation injury could be functionally mitigated by AAT exposure. In part, it may function by decreasing amplification damage promoted by TNF and IL-1b production.

Example 2

This exemplary method describes the use of a Mixed Lymphocyte culture (MLC) to assess the effect of AAT in an in vitro model of Graft-versus-Host Disease (GVHD).

Methods and Materials:

MLCs were used to assess alloreactivity as a simple in vitro model of GVHD. Human PBMC were suspended in RPMI 1640 medium supplemented with 1% nonessential amino acids; 1% sodium pyruvate; 1% L-glutamine; and 10% heat-inactivated, pooled, normal human serum. One×10⁵ responder cells and 1×10⁵ irradiated (2,200 cGy) stimulator cells per well were co-cultured in triplicate in round-bottom 96-well plates for 6 days at 37° C. in a humidified 5% carbon dioxide/air atmosphere. MLCs were carried out either in unmodified medium or with the addition of AAT (at concentrations of 0.1 to 0.5 mg/ml) or albumin. All final culture volumes were 200 µl/well. Concanavalin A (Sigma-Aldrich Co. St. Louis, Mo.) was added (4 µg/well) on day 3 to responder cells plated without stimulator cells to provide a control for cell proliferation. On day 6, cultures were pulsed with 1 µCi of ³H-thymidine for 18 hours before harvesting; ³H-thymidine uptake was measured as the mean counts per minute (cpm) from the three replicates and harvested onto filter paper strips using a [beta]-scintillation counter (Packard BioScience Company, Meriden, Conn.). Results were expressed as stimulation index (SI)=(mean cpm of stimulated cells−mean cpm of nonstimulated cells: mean cpm of non-stimulated cells).

Supernatants from MLCs were collected and analyzed for cytokines and other markers (e.g. inflammatory) with potential relevance to GVHD, including TNF-α, IL-6 and IL-8, as determined by enzyme-linked immunosorbent assays (ELISA). The probes used included human BAF210 TNF-α, BAF206 IL-6, BAF208 IL-8 (R&D Systems, Minneapolis, Minn.). When inflammatory marker concentrations were less than the assay detection limit, the sample was assigned the median value between 0 and the detection limit.

RNA Interference (RNAi) and Transient Transfection

Stealth siRNA oligonucleotides, specifically designed to silence the expression of all IL32 isoforms, were obtained from Invitrogen (Carlsbad, Calif.). PBMC from healthy donors (1×10⁶) were electroporated with 500 ng of siRNA by nucleofection (Human Cell Nucleofector kit, Program V-024, Amaxa Biosystems, Cologne, Germany). The siRNAs had the following sequences:

```
Scrambled:
                                SEQ ID NO: 41
5'-CGAAUCCUAAUGCUGCUCCCUACUU-3'
and

SEQ ID NO: 42
3'-AAGUAGGGAGGAGCAUUACCAUUCG-5'.

IL-32 specific -
                                SEQ ID NO: 43
5'-CUUUGGUGCCAACUCUGCCUCUCUU-3'
and

SEQ ID NO: 44
3'-AAGAGAGGCAGAGUUGGCACCAAAG-5.
```

Human Cytokine Protein Array

After transfection with either scrambled or IL32-specific siRNA, PBMC were cultured for 96 hours in RPMI 1640 medium, containing 5% fetal bovine serum (FBS), and penicillin/streptomycin (P/S) (50 U/ml and 50 µg/ml, respectively), and supernatants were collected. To determine the presence of various cytokines, we used the human proteome profiler array membrane kit Panel A (ARY005; R&D Systems, Minneapolis, Minn.; USA) according to the manufacturer's instructions. Equal volumes (1 ml) of supernatant were collected from cultured PBMC and added to the pre-coated membranes of the kit. The dot blot membranes (standardized for loading control) were analyzed using ImageQuant software (Molecular Dynamics, Sunnyvale, Calif.).

Analysis of Human and Murine Cytokines by Real-Time PCR

RNA was extracted by standard techniques. Applied Biosystems Pre-Designed Gene Expression Assays containing both primers and fluorescent Taq-Man probes were used to determine human or mouse gene expression. β-actin and GUSB were used as 'housekeeping' controls for normalization of quantitative RNA variation.

Human probes: IL-32, all isoforms (Hs00170403_m1), IL-32 β and ε isoforms (Hs00997068_g1), IL-32 α and γ (Hs00992439_g1), β-actin, (Hs00607939), GUSB (Hs03929099_m1), TNFα (Hs00174128_m1), IL-1β (Hs01555410_m1), PR3 (Hs01597752_m1), PAR2 (Hs00173741_m1).

Murine probes: TNFα (Mm00443258_m1), IL-1β (Mm01336189_m1), IL-1Ra (Mm01337566_m1) and PR3 (Mm00478323_m1).

Each 20 µL reaction contained 2.0 µL 10×PCR Buffer without Mg2+, 2.8 µL 25 mM $MgCl_2$ (3.5 mM final concentration), 0.4 µL ROX passive reference dye, 0.4 µL 10 mM dNTPs, 1.0 µL ABI primer/probe, and 0.16 µL (0.8 U) Fast Start Taq Polymerase (Roche, Indianapolis, Ind., USA), 8.24 µL $H_2O$ and 5 µL of the cDNA template. All reactions were carried out in triplicate in 384-well plates on an ABI7900HT (Applied Biosystems, Carlsbad, Calif.). For inclusion in the data set, standard deviations of the triplicates had to be less than 0.15 CT (cycle threshold). Additionally, PCR efficiencies of the ABI assays were verified at >95% and that the slopes of the linear portion of the amplification curves varied by less than 5%.

IL-32 Expression in MLC

To determine a potential role of IL-32 in MLC reactivity, we processed responder cells from MLC for western blotting and RNA analysis. PBMC were cultured for 7 days, and western blots were generated either from unsorted or sorted CD8+ responder cells; one blot is representative of 3 similar experiments. FIG. 5A represents a Western blot of unsorted PBMC responder cells or sorted CD8+ responder cells isolated from allogeneic MLC cultures showing the protein levels of γIL-32, βIL-32, and the β-actin control, wherein the "x" symbol refers to irradiated cells, and "A" refers to donor A, and "B" refers to donor B. For example, "A+Ax" refers to Donor A versus Donor A with irradiated cells (no allogeneic reaction).

FIG. 5B graphically illustrates the IL-32 mRNA levels in allogeneic MLC. Error bars represent mean±SEM of 3 similar experiments. Solid columns represent results in allogeneic cultures, open columns represent results in autologous controls. The results are displayed as ±SEM from 3 similar experiments. * indicates $p<0.01$ (Student t test). FIG. 5C graphically illustrates the protein levels of TNFα in allogeneic MLC as determined by ELISA assay. Error bars represent mean±SEM of 3 similar experiments. Solid columns represent results in allogeneic cultures, open columns represent results in autologous controls. FIG. 5D graphically illustrates the protein levels of IL-6 in allogeneic MLC as determined by ELISA assay. Error bars represent mean±SEM of 3 similar experiments. Solid columns represent results in allogeneic cultures, open columns represent results in autologous controls. FIG. 5E graphically illustrates the protein levels of IL-8 in allogeneic MLC as determined by ELISA assay. Error bars represent mean±SEM of 3 similar experiments. Solid columns represent results in allogeneic cultures, open columns represent results in autologous controls.

As shown in FIGS. 5A and 5B, IL-32 was upregulated both at the mRNA and protein levels in cells exposed to allogeneic stimulator cells in comparison to autologous controls. The supernatants of the same 7-day MLCs revealed high levels of TNF-α (FIG. 5C), IL-6 (FIG. 5D), and IL-8 (FIG. 5A).

Repression of IL-32 by siRNA or Addition of AAT Broadly Inhibits Inflammatory Mediators To study the role of endogenous IL-32 in PBMC, IL-32-specific siRNA oligomers were used, which target each of the IL-32 isoforms as confirmed by BLAST (basic local alignment search tool) alignment. FIG. 6A graphically illustrates the change in a panel of various cytokines expressed in PBMC transfected with IL-32 specific or scrambled siRNA (control), expressed as percent change in comparison to control supernatants. As illustrated in FIG. 6A, it was determined that down-regulation of IL-32 by siRNA resulted in a global reduction of cytokine levels in the supernatants, as illustrated by the array of 36 cytokines. One cytokine that was up-regulated (by 56% and 60% in two biological duplicates) was 1-309, a chemokine secreted by regulatory T cells.

To determine the impact of AAT on IL-32 protein levels, human stroma cell line HS5 was used, which expresses and secretes IL-32 and can be grown in serum-free medium previously shown. FIG. 6B represents a Western blot of protein extract of the human stroma cell line HS5 exposed to vehicle only (veh) or various concentrations of AAT (in serum-free medium). Levels of IL-32 β and γ isoforms at concentrations of ATT between 0.1 and 1 mg/ml are illustrated. This blot is representative of 3 similar experiments. As illustrated in FIG. 6B, the introduction of AAT (at 0.1-1.0 mg/ml) to the cells resulted in reductions of endogenous IL-32β and γ isoforms.

IL-32 and AAT Effect on Secreted Cytokines in MLC

In another example, MLC which AAT was added at concentrations ranging from 0.1 to 0.5 mg/ml were examined FIG. 7 illustrates inhibition of proliferation and TNFα secretion in MLC by AAT.

FIG. 7A illustrates some of the results using a Western blot analysis of IL-32β and γ levels in CD8+ cells from 7-day MLCs under control conditions and in the presence of AAT (0.3 mg/ml). The Western blot is representative of 3 similar experiments.

FIG. 7B graphically illustrates the expression changes in IL-32 protein levels in allogeneic MLCs and autologous controls as determined by densitometry (OD) of the same biological experiment. Open columns reflect results in the absence of AAT; solid columns in the presence of AAT.

FIG. 7C graphically illustrates proliferation in MLC (as measured by $^3$H thymidine uptake; CPM, mean±SEM) in the presence of various concentrations of AAT. FIG. 7D graphically illustrates the results of a TNF-α ELISA assay measuring the secretion of TNF a in the presence and absence of AAT. * indicates p<0.05 (Student t test).

As illustrated in FIG. 7A-7D, CD8+ cells sorted from MLCs to which AAT was added showed levels of IL-32β and γ isoforms at least 2-fold lower than in the absence of AAT. Concurrently, there was significant dose-dependant suppression of the proliferative capacity as determined by $^3$H thymidine uptake and a 2-fold reduction in TNFα levels. These data demonstrate that AAT had a profound effect on reducing alloreactivity in parallel with inhibition of IL-32 and TNFα production.

This data illustrates that AAT strongly suppressed CD8+ cell proliferation in allogeneic MLCs, and inhibition of proliferation was associated with suppression of IL-32, as well as other pro-inflammatory proteins, such as TNF-α, IL-8 and IL-6. AAT has cytoprotective activities as illustrated by these experiments.

Example 3

This Example illustrates effects of AAT on survival and prevention of GVHD in mice that are irradiated in the context of an MHC matched, minor antigen disparate murine transplant model.

In another exemplary experiment, the experiment focused on determining involvement of interleukin (IL)-32 in the "cytokine storm" that has been described in the peri- and post-hematopoietic cell transplantation (HCT) period. Tumor necrosis factor α (TNF), is consistently upregulated in transplant recipients, is a potent inducer of IL-32. Conversely, IL-32 has been shown to induce TNF, suggesting the possibility of an amplification loop between these two cytokines. IL-32 was originally identified in IL-2-activated T lymphocytes and natural killer (NK) cells supporting a potential role in T-cell activation and function following allogeneic HCT. Furthermore, IL-32 is present in supernatants of IL-12-, IL-18-, and IL-12-plus IL-18-stimulated human NK cells and in the supernatant of concanavalin A-stimulated human peripheral blood mononuclear cells (PBMC). Additionally, in patients with myelodysplastic syndrome, it was previously reported that silencing of endogenous IL-32 had other benefits.

As demonstrated in Examples 1 and 2, suppression of endogenous IL-32 in a variety of models consistently correlated with a reduction in TNF-α levels and other cytokines. Gene expression studies in human marrow stroma cells demonstrated that IL-32 was induced by TNF-α, a cytokine that is centrally involved in GVHD. IL-32 expression increases upon differentiation of T cells. Such a pattern would be consistent with the present findings, which illustrate a correlation of IL-32 expression with responses in MLC and with the manifestations of acute GVHD. As IL-32 has pro-apoptotic activity and can upregulate TNF-α, its expression may contribute to target organ damage. Although IL-32 is produced locally, the cytokine was readily detected in the systemic circulation, and IL-32 mRNA concentrations in PBMC discriminated between patients with and without acute GVHD. Therefore, the following experiment was carried out to determine whether inhibition of IL-32 activation would interfere with alloactivation and possibly prevent or attenuate the development and manifestations of GVHD.

Methods:

C57/BL6J mice (H-$2^b$) (Jackson Laboratory, Bar Harbor, Me.), 10-14 weeks old with average body weight of 28 g, received single-dose total body irradiation with 1000 cGy followed by intra-tail vein injection of T-cell-depleted bone marrow (BM, 5×10$^6$ cells), and CD8+ splenic lymphocytes (0.2×10$^6$ cells) from C3H.SW-H$2^b$/SnJ donors)(H-$2^{bc}$) (Jackson Laboratory, Bar Harbor, Me.). BM was T-cell-depleted using the T Cell Isolation Kit II (Milteny Biotec, Auburn, Calif.). CD8+ T-cells were isolated from splenocytes by positive selection, using MACS CD8+ microbeads as directed by the manufacturer (Milteny Biotec, Auburn, Calif.).

Mice in the experimental group were given AAT intraperitoneally at 3 mg/dose, suspended in 125 µl, 24 hours before irradiation (Day −1) and donor cell infusion, and every 2 days post-HCT for a total of 10 injections. Mice in the control group were injected, also intra-peritoneally, with 125 µl of human albumin on the same schedule. Each group consisted of 16 mice. GVHD was assessed by a standard scoring system (Cooke, K. R., et al., *Blood* 88:3230-3239, 1996).

Body weights were obtained and recorded on day 0 and weekly thereafter. A weekly clinical index was generated by summation of 5 criteria scores: percentage of weight change, posture (hunching), activity, fur texture, and skin integrity (maximum score=10). Animals that received a score of 6.5 or higher were killed using $CO_2$ euthanasia. Blood samples were collected sequentially for cytokine assays. To determine the presence of various cytokines in the two groups of mice, we used the mouse proteome profiler array membrane kit Panel A (ARY006; R&D Systems, Minneapolis, Minn.) according to the manufacturer's instructions. Equal volumes (100 μl) of plasma were collected from individual animals and added to the precoated membranes of the kit. The dot blot membranes (standardized for loading control) were analyzed using ImageQuant software (Molecular Dynamics, Sunnyvale, Calif.).

Chimerism Analysis

Then, chimerism analyses were performed on mouse PBMC following separation of blood on Ficoll-Hypaque (density=1.074) (Graves, S. S., et al., "Stable Trichimerism After Marrow Grafting From 2 DLA-Identical Canine Donors and Nonmyeloablative Conditioning," Blood 110: 418-423, 2007). Cells at the interface were collected and washed in phosphate buffered saline by centrifugation. The contributions of recipient (C57/BL6J) and donor cells (C3H.SW-H$2^b$/SnJ) to peripheral blood were quantified by fluorescent variable number of tandem repeat (VNTR) PCR analysis, as previously described.

Results:

AAT reduces mortality and abrogates GVHD in irradiated mice receiving an MHC matched, minor antigen disparate transplant.

The lethally irradiated (1000 cGy) C57/BL6J (H-$2^b$) mice were injected intravenously (iv) with 5×10$^6$ T cell-depleted BM cells and 0.2×10$^6$ CD8+ splenic T cells from C3H.SW-H$2^b$/SnJ mice (H-$2^{bc}$). Recipient mice were given 3 mg of AAT (in 125 μL) on day −1 and again on day +2 and every 72 hours for a total of 10 injections.

FIG. 8A graphically illustrates the percent survival of AAT-treated mice versus albumin-treated control mice (n=15 for each group, p=0.04). As shown in FIG. 8A, by day 65 after transplantation, survival was 80% in AAT-treated mice versus 40% in albumin treated controls (n=15; p=0.04, log rank).

FIG. 8B graphically illustrates the severity of GVHD in the AAT-treated mice versus the albumin-treated control mice. GVHD was scored based on percentage of weight loss, skin integrity, posture, mobility, and fur texture. Clinical signs were graded on a scale of 0 to 2, where 0 was absent, 1 was moderate, and 2 was severe, and the individual scores were added up. Illustrated are GVHD clinical scores for 30 days after transplantation (mean±SEM per time point). As illustrated in FIG. 8B, Albumin controls showed higher GVHD scores than AAT treated mice. Two AAT-treated mice that developed signs of gut-GVHD by day 45, i.e., after discontinuation of AAT, showed complete resolution of GVHD upon re-institution of AAT therapy, given every 72 hours, for 4-5 doses.

FIG. 8C graphically illustrates the change in body weight of transplanted AAT-treated mice and albumin-treated mice over time post-transplant (mean±SEM; n=15). As illustrated in FIG. 8C, Albumin controls experienced significantly greater weight loss and showed higher GVHD scores than AAT treated mice.

FIG. 8D graphically illustrates the proportion of donor cells among PBMC in AAT-treated (n=6) versus albumin-treated (n=5) mice at day 45 (p=0.25). As shown in FIG. 8D, in both albumin controls and AAT-treated mice C3H.SW-H$2^b$/SnJ donor cells accounted for more than 95% of cells in peripheral blood (p=0.25).

Histologic examination of albumin-treated mice showed patchy epithelial damage in the hair follicles and edema. The forestomach and duodenum showed patchy lymphocytic infiltration of epithelium and damage to the glands as evidenced by exocytosis and apoptosis (data not shown). Mice treated with AAT, in contrast, had normal skin and only rare areas of infiltration in stomach and duodenum (data not shown). These results indicate that AAT significantly attenuated clinical and histologic manifestations of radiation-induced toxicity and reduced GVHD-related morbidity and mortality.

AAT Suppresses Pro-Inflammatory Signals and Upregulates IL-1Rα in MHC Matched, Minor Antigen Disparate Murine Transplant Recipients FIG. 9 graphically illustrates the effect of AAT on cytokine RNA and protein expression in PBMC and plasma 21 days after transplantation. FIG. 9A graphically illustrates the log 2 change in RNA levels of IL-1Rα, IL-1β, TNF-α, and PR3 in PBMC, as determined by RT-PCR. The RNA levels in AAT-treated mice (n=6) ate expressed relative to levels in albumin-treated controls; mean±SEM (n=6) (log 2). As shown in FIG. 9A, steady-state levels of IL-1β, TNF-α, and PR3 mRNA on day 21 was significantly lower in AAT-treated compared to albumin-treated animals.

FIGS. 9B-9D graphically illustrate the mean±SEM cytokine plasma levels at 3, 7 and 10 days after transplantation. Illustrated is a panel selected from a mouse array of 40 cytokines, showing significant changes. Changes in cytokine concentration are expressed as percent change compared to albumin control. The horizontal dotted line indicates an increase/decrease of 25%. As shown in FIGS. 9B-9D, in a panel of 40 cytokines there was a global suppression of cytokine levels except for IL-1Rα in the plasma of AAT-treated mice. Also suppressed were, among others, factors such as CXCL13/BLC/BCA-1, a B cell-attracting chemokine 1(BCA-1), and CXCL2/MIP-2, known as macrophage inflammatory protein 2-α (MIP2-α), a chemokine chemotactic for polymorphonuclear leukocytes.

The in vivo results in this Example illustrate that treatment with AAT suppresses radiation-related cytokine release and activation of allogeneic T lymphocytes, which in turn may be associated with attenuation or prevention of GVHD, entirely consistent with preferential development of T regs. In addition, AAT administration suppressed GVHD manifestations even in mice that showed flares of GVHD following discontinuation of prophylactic ATT, suggests that this compound was also effective in inhibiting "downstream" events following activation of allogeneic T lymphocytes. Alternatively, the benefit of AAT in that setting may be related to inhibition of IL-32 activation in other tissues, e.g., epithelial cells. Thus, IL-32 plays a central role in alloreactivity and GVHD. Results support that hypothesis and show that administration of AAT profoundly affected expression of IL-32.

These results illustrate that after allogeneic hematopoietic cell transplantation, IL-32 mRNA levels in blood leukocytes were statistically significantly higher in patients with acute GVHD (n=10) than in serial samples from patients who did not develop acute GVHD (n=5; p=0.02). No significant changes in IL-32 levels were present in patients with treated (n=14) or untreated (n=8) chronic GVHD, compared to healthy controls (n=8) (p=0.5 and p=0.74, respectively).

It has been demonstrated herein that the addition of α-1 anti-trypsin (AAT) or molecules having similar activities, which interferes with the processing of IL-32 by PR3, other activity leads to decreased proliferation of cells in MLC, reduced cytokine production, and also may be used as a radioprotectant to reduce or prevent cellular damage induced by radiation exposure in a mammalian subject in need thereof.

Example 4

In one exemplary method, a 60 year old man is diagnosed with prostate cancer and decides to undergo therapy with external beam irradiation. The therapy involves administration of a fractionated dose of radiation delivered three times per week for 6-8 weeks. The expected, common acute side effects of this therapy are 1: inflammation of the rectum and anus with discomfort, pain, friable rectal mucosa and rectal bleeding; 2. bladder dysfunction with dysuria, frequency, pain and hematuria, and 3. erective dysfunction. The most common chronic side effects are erectile dysfunction and incontinence, although bowel obstruction and/or urinary obstruction can occur.

In this example, treatment with a composition including AAT or AAT fragments or recombinant or mutant AAT molecules, can be administered as a pharmaceutically acceptable composition by a weekly infusion of AAT at a dose of about 40 to about 120 mg/kg iv commencing prior to the first dose of radiation therapy and continuing for up to 4 weeks following completion of the radiation therapy. Administration of these compositions will result in a marked decrease in both acute and chronic side effects of the radiation therapy. The patient will have minimal rectal and bladder dysfunction and will have minimal or no loss in sexual (erectile) function as a result of the radiation therapy. In addition the use of AAT in combination with radiation therapy will result in the same or higher level of tumor eradication as can be accomplished by radiation therapy alone. Finally, with the greater protection of injury to bowel, bladder and nerve tissue adjacent to prostate, it will be possible to increase the dose of radiation or decrease the number of fractions to achieve the treatment in a shorter interval of time and/or increase the efficacy of the therapy in terms of tumor eradication.

Example 5

In another exemplary method, an individual is accidentally exposed to a large dose of whole body irradiation, for example, by a radiation leak at a factory. Currently, there are few to no therapies for this type of radiation exposure. One of the only available medical therapies is to administer a high dose of iodine to block uptake of radioactive species into the thyroid and to physically remove the offending radioactive materials by washing or cleansing. Tissues most sensitive to whole body irradiation are the bone marrow and the bowel, and even relatively low levels of accidental irradiation can result in severe immunodeficiency, severe bowel dysfunction and death. The injury begins with the initial exposure to the radiation dose, but continues over days and weeks into weeks of tissue damage.

Immediate and supplemental treatment with AAT can block or reduce the reactions initiated by the irradiation. In the case of the individual accidentally overexposed to radiation the treatment with AAT should begin as early as possible, but would be expected to have a beneficial effect up to 1-2 weeks or even a month following irradiation. AAT should be administered at a dose of about 40 to about 120 mg/kg by I.V. before (if possible) during or after such exposure. infusion or other mode as soon as possible following the irradiation and then continued by weekly infusions or doses for 8-12 weeks. AAT would be expected to markedly decrease the effects of the irradiation and tissue damage, with the final result being dependent on the magnitude of the dose of radiation received. All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A method for ameliorating adverse effects of radiation exposure in a subject comprising, administering to a subject undergoing or scheduled to undergo radiation therapy a therapeutically effective amount of a composition comprising alpha-1 antitrypsin (AAT), a fragment thereof or a mutant thereof wherein the composition ameliorates the adverse effects of the radiation therapy in the subject.

2. The method of claim 1, wherein the composition comprises naturally occurring AAT (SEQ ID NO:1 or SEQ ID NO:39).

3. The method of claim 1, wherein the composition comprises a composition of one or more carboxyterminal fragments of naturally occurring AAT.

4. The method of claim 1, wherein the subject is undergoing radiation therapy for a condition.

5. The method of claim 4, wherein the condition is cancer.

6. The method of claim 1, wherein the subject has been exposed to radiation as a result of a nuclear accident, nuclear test or nuclear attack.

7. The method of claim 1, wherein the subject has undergone, or is undergoing a diagnostic procedure that comprises exposure to radiation.

8. The method of claim 1, wherein the composition is administered in a therapeutically effective amount to reduce or prevent at least one radiation-induced effect selected from the group consisting of myelosuppression, renal toxicity, weight loss, behavioral changes, pain, nausea, vomiting, diarrhea, constipation, anemia, malnutrition, hair loss, numbness, changes in tastes, loss of appetite, thinned or brittle hair, mouth sores, memory loss, hemorrhage, cardiotoxicity, hepatotoxicity, ototoxicity, and post-chemotherapy cognitive impairment, or a combination thereof.

9. The method of claim 8, wherein the behavioral change is limited mobility.

10. The method of claim 1, wherein the subject is a human subject.

11. The method of claim 1, wherein the composition is administered to the subject in an amount effective to reduce or prevent cellular damage induced by the radiation exposure.

12. The method of claim 1, wherein the therapeutically effective amount of the composition comprises a single intravenous infusion in the subject of AAT at a dose of 1 mg/kg to 150 mg/kg, optionally followed by additional treatments with the composition.

13. The method of claim 1, wherein the therapeutically effective amount of the composition comprises a concentration of AAT of 1 mg/kg to about 150 mg/kg, before, during or after radiation therapy.

14. The method of claim 1, wherein the therapeutically effective amount of the composition comprises a concentration of AAT of 1 mg/kg to about 100 mg/kg administered to the subject every 24 to 48 hours after radiation therapy up to a predetermined time period.

15. The method of claim 1, wherein the administration comprises at least two doses of AAT from about 40 to 80 mg/kg every 24 to 48 hours for a period of from 2 days to 30 days after radiation exposure.

16. The method of claim 1, wherein the radiation exposure comprises an acute or chronic dose of ionizing or non-ionizing radiation.

17. The method of claim 16, wherein the ionizing radiation comprises X-rays.

18. The method of claim 16, wherein the ionizing radiation comprises radio nuclides.

19. The method of claim 7, wherein the diagnostic procedure comprises X-rays, a CATscan, a mammogram, a radionuclide scan or an interventional radiological procedure under CT or fluoroscopy guidance.

20. A method for ameliorating adverse effects of exposure to whole body radiation comprising, administering to a subject having been exposed to whole body radiation a therapeutically effective amount of a composition comprising alpha-1 antitrypsin (AAT), a fragment thereof, a recombinant molecule thereof or a mutant thereof wherein the composition ameliorates the adverse effects of the radiation in the subject.

21. The method of claim 20, wherein the composition comprises naturally occurring AAT (SEQ ID NO:1 or SEQ ID NO:39).

22. The method of claim 20, wherein the composition comprises a composition of one or more carboxyterminal fragments of naturally occurring AAT.

23. The method of claim 20, wherein the therapeutically effective amount of the composition comprises a single intravenous infusion in the subject of AAT at a dose of about 1 mg/kg to about 150 mg/kg, optionally followed by additional treatments with the composition.

24. The method of claim 20, further comprising analyzing samples from the subject for levels of active agents after administration.

25. The method of claim 20, wherein the composition is administered to the subject within the first 48 hours of the exposure.

26. The method of claim 20, wherein the composition is administered to the subject several days after the exposure.

27. The method of claim 20 wherein the composition is administered to the subject daily for several days after the exposure.

\* \* \* \* \*